(12) United States Patent
Audia et al.

(10) Patent No.: US 7,648,983 B2
(45) Date of Patent: Jan. 19, 2010

(54) BACE INHIBITORS

(75) Inventors: James Edmund Audia, Zionsville, IN (US); Dustin James Mergott, Zionsville, IN (US); Scott Martin Sheehan, Carmel, IN (US); Brian Morgan Watson, Carmel, IN (US)

(73) Assignee: Eli Lilly and Company, Indianapolis, IN (US)

(*) Notice: Subject to any disclaimer, the term of this patent is extended or adjusted under 35 U.S.C. 154(b) by 0 days.

(21) Appl. No.: 12/423,918

(22) Filed: Apr. 15, 2009

(65) Prior Publication Data

US 2009/0275566 A1    Nov. 5, 2009

Related U.S. Application Data

(60) Provisional application No. 61/049,881, filed on May 2, 2008.

(51) Int. Cl.
C07D 417/02 (2006.01)
A61K 31/541 (2006.01)
A61P 25/28 (2006.01)

(52) U.S. Cl. ...................... 514/227.2; 544/45
(58) Field of Classification Search .......... 544/45; 514/227.2

See application file for complete search history.

(56) References Cited

FOREIGN PATENT DOCUMENTS

| EP | 0717040 A1 | 6/1996 |
|---|---|---|
| WO | WO 96/14842 | 5/1996 |
| WO | WO 2007/049532 A1 | 5/2007 |
| WO | WO 2008/133273 A1 | 11/2008 |
| WO | WO 2008/133274 A1 | 11/2008 |

OTHER PUBLICATIONS

Evin et al; BACE Inhibitors as Potential Therapeutics for Alzheimer's Disease, Recent Patents on CNS Drug Discovery, 2007, vol. 2, pp. 188-199.

Pasteur et al; boom in the Development of Non-Peptidic Beta-Secretase (BACE1) Inhibitors for the Treatment of Alzheimer's Disease, Medicinal Research Reviews, vol. 29, No. 2, 2009, pp. 295-338.

*Primary Examiner*—Kahsay T Habte
(74) *Attorney, Agent, or Firm*—Elizabeth A. Dingess-Hammond

(57) ABSTRACT

The present invention provides BACE inhibitors of Formula I:

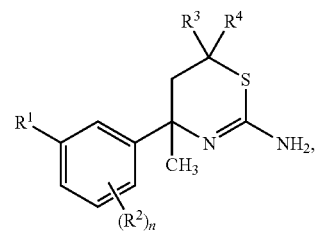

methods for their use, and intermediates and methods for their preparation.

13 Claims, No Drawings

BACE INHIBITORS

This application claims the benefit of U.S. Provisional Application No. 61/049,881, filed May 2, 2008.

The present invention is in the field of treatment of Alzheimer's disease and other diseases and disorders involving amyloid β (Aβ) peptide, a neurotoxic and highly aggregatory peptide segment of amyloid precursor protein (APP). Specifically provided are potent inhibitors of β-secretase or β-site amyloid precursor protein-cleaving enzyme (BACE). Complete or partial inhibition of BACE has been shown to have a significant effect on plaque-related and plaque-dependent pathologies in mouse models suggesting that even small reductions in Aβ levels might result in long-term significant reduction in plaque burden and synaptic deficits, thus providing significant therapeutic benefits.

Currently described BACE inhibitors are peptidomimetic transition state analogs, typically containing a hydroxyethyl moiety. Although many of these compounds are potent inhibitors of BACE, their high molecular weights and low membrane permeability make them poor drug candidates. There has been a progression from large peptidomimetic molecules to small molecules, such as a variety of hydroxyethylamine scaffolds as well as heterocyclic-containing scaffolds. See e.g. Durham and Shepherd, *Current Opinion in Drug Discovery & Development*, 9(6), 776-791 (2006)). Certain aminothiazine compounds have been described as BACE inhibitors in WO 2007/049532.

BACE inhibitors that are potent and more efficacious are necessary to provide treatments for Aβ peptide-mediated disorders, such as Alzheimer's disease. The present invention provides new potent and efficacious inhibitors of BACE.

The present invention provides compounds of Formula I:

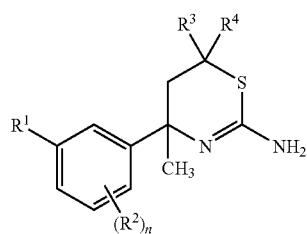

where:
n is 0, 1, or 2;
$R^1$ is pyrimidinyl, pyrazinyl optionally substituted with chloro or fluoro, or pyridinyl optionally substituted with one or two substituents each independently selected from chloro, fluoro, and $C_1$-$C_3$ alkoxy;
$R^2$ is at each instance independently selected from chloro and fluoro;
$R^3$ is hydrogen or $C_1$-$C_4$ alkyl optionally substituted with hydroxy; and
$R^4$ is hydrogen or $C_1$-$C_3$ alkyl;
or a pharmaceutically acceptable salt thereof.

The present invention also provides a method of treating Alzheimer's disease in a patient comprising administering to a patient in need of such treatment an effective amount of a compound of Formula I.

The present invention further provides a method of preventing the progression of mild cognitive impairment to Alzheimer's disease in a patient comprising administering to a patient in need of such treatment an effective amount of a compound of Formula I.

The present invention further provides a method of preventing the progression in a patient at risk for developing Alzheimer's disease comprising administering to a patient in need of such treatment an effective amount of a compound of Formula I.

The present invention also provides a method of inhibiting BACE in a patient comprising administering to a patient in need of such treatment an effective amount of a compound of Formula I.

The present invention also provides a method for inhibiting β-secretase mediated cleavage of amyloid precursor protein comprising administering to a patient in need of such treatment an effective amount of a compound of Formula I.

The present invention further provides a method for the inhibition of production of Aβ peptide comprising administering to a patient in need of such treatment an effective amount of a compound of Formula I.

The present invention also provides a pharmaceutical formulation comprising a compound of Formula I, in combination with a pharmaceutically acceptable carrier, diluent, or excipient.

Furthermore, this invention provides a compound of Formula I for use in therapy, in particular for the treatment of Alzheimer's disease or for the prevention of the progression of mild cognitive impairment to Alzheimer's disease. This invention also provides the use of a compound of Formula I for the manufacture of a medicament for the treatment of Alzheimer's disease. This invention further provides the use of a compound of Formula I for the manufacture of a medicament for the prevention of the progression of mild cognitive impairment to Alzheimer's disease. The invention also provides the use of a compound of Formula I for the manufacture of a medicament for the inhibition of BACE. The invention further provides the use of a compound of Formula I for the manufacture of a medicament for the inhibition of production of Aβ peptide.

Additionally, this invention provides a pharmaceutical formulation adapted for the treatment of Alzheimer's disease. Furthermore, this invention provides a pharmaceutical formulation adapted for the prevention of the progression of mild cognitive impairment to Alzheimer's disease. This invention also provides a pharmaceutical formulation adapted for the inhibition of BACE.

Furthermore the present invention provides a pharmaceutical formulation adapted for the inhibition of β-secretase mediated cleavage of amyloid precursor protein. The present invention also provides a pharmaceutical formulation adapted for the treatment of conditions resulting from excessive levels of Aβ peptide comprising a compound of Formula I or a pharmaceutically acceptable salt thereof in combination with one or more pharmaceutically acceptable excipients, carriers, or diluents.

The general chemical terms used in the formulae above have their usual meanings. For example, the term "$C_1$-$C_3$ alkyl" refers to methyl, ethyl, propyl, and isopropyl. The term "$C_1$-$C_4$ alkyl" refers to methyl, ethyl, propyl, isopropyl, butyl, isobutyl, sec-butyl, and tert-butyl moieties.

"$C_1$-$C_4$ alkyl optionally substituted with hydroxy" is a $C_1$-$C_4$ alkyl group wherein one of the hydrogen atoms is replaced with a hydroxy moiety.

The term "$C_1$-$C_3$ alkoxy" is a $C_1$-$C_3$ alkyl group bonded to an oxygen atom and refers to methoxy, ethoxy, propoxy, and iso-propoxy.

The term "nitrogen protecting group" is taken to mean a moiety that is stable to projected reaction conditions and yet may be selectively removed by reagents and reaction conditions compatible with the regenerated amine. Such groups are well known by the skilled artisan and are described in the literature. See, e.g., Greene and Wuts, *Protective Groups in Organic Synthesis*, Third Edition, Chapter 7, John Wiley and Sons Inc., (1999).

The term "inhibition of production of Aβ peptide" is taken to mean decreasing of in vivo levels of Aβ peptide in a patient to normal, if excessive, or sub-normal levels, as required.

The term "effective amount of a compound of Formula I" is taken to mean the dose or doses of a compound of Formula I required to inhibit BACE sufficiently to decrease in vivo levels of Aβ peptide in a patient to normal or sub-normal levels.

The term "treatment" is taken to include slowing or arresting the progression of the disease in a patient.

Mild cognitive impairment has been defined as a potential prodromal phase of dementia associated with Alzheimer's disease based on clinical presentation and on progression of patients exhibiting mild cognitive impairment to Alzheimer's dementia over time. (Morris, et al., *Arch. Neurol.*, 58, 397-405 (2001); Petersen, et al., *Arch. Neurol.*, 56, 303-308 (1999)). The term "prevention of the progression of mild cognitive impairment to Alzheimer's disease" includes slowing, arresting, or reversing the progression of mild cognitive impairment to Alzheimer's disease in a patient.

The skilled artisan will appreciate that compounds of Formula I can exist in tautomeric forms, as depicted in FIG. (1). When any reference in this application to one of the specific tautomers of the compounds of formula I is given, it is understood to encompass both tautomeric forms and all mixtures thereof.

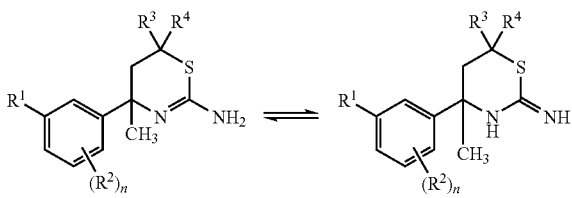

Figure (1)

The skilled artisan will appreciate that compounds of Formula I are comprised of a core that contains at least one chiral center:

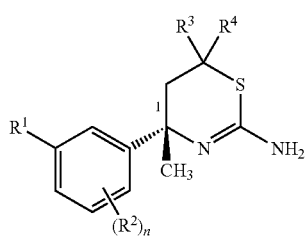

FIG. (2)

Although the present invention contemplates all individual enantiomers, as well as mixtures of the enantiomers of said compounds including racemates, the compounds with the absolute configuration at the atom labeled 1 as illustrated in FIG. (2) are preferred compounds of Formula I.

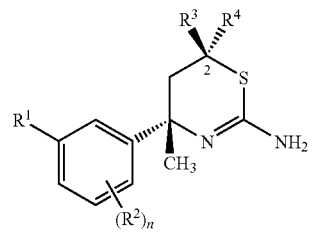

FIG. (3)

Further, when appropriately substituted, the compounds with the absolute configuration of the atom labeled 2, as illustrated in FIG. (3), are preferred compounds of Formula I.

Additionally, the skilled artisan will appreciate that additional chiral centers may be created in the compounds of the invention by the selection of certain variables. The present invention contemplates all individual enantiomers or diastereomers, as well as mixtures of the enantiomers and diastereomers of said compounds including racemates.

The skilled artisan will also appreciate that the Cahn-Ingold-Prelog (R) or (S) designations for all chiral centers will vary depending upon the substitution patterns of the particular compound. The single enantiomers or diastereomers may be prepared beginning with chiral reagents or by stereoselective or stereospecific synthetic techniques. Alternatively, the single enantiomers or diastereomers may be isolated from mixtures by standard chiral chromatographic or crystallization techniques at any convenient point in the synthesis of compounds of the invention. Single enantiomers and diastereomers of compounds of the invention are a preferred embodiment of the invention.

The compounds of the present invention are amines, and accordingly react with any of a number of inorganic and organic acids to form pharmaceutically acceptable acid addition salts. Pharmaceutically acceptable salts and common methodology for preparing them are well known in the art. See, e.g. P. Stahl, et al. *Handbook of Pharmaceutical Salts: Properties, Selection and Use*, (VCHA/Wiley-VCH, 2002); S. M. Berge, et al., "Pharmaceutical Salts," *Journal of Pharmaceutical Sciences*, Vol. 66, No. 1, January 1977. Preferred pharmaceutically acceptable salts are those formed with hydrochloric acid.

Although all of the compounds of Formula I are useful inhibitors of BACE, certain classes of compounds are preferred. The following paragraphs describe such preferred classes:

a) $R^1$ is pyrimidinyl;
b) $R^1$ is pyrazinyl optionally substituted with fluoro;
c) $R^1$ is pyridinyl optionally substituted one or two times at each instance independently selected from chloro, fluoro, or methoxy;
d) $R^1$ is pyridinyl optionally substituted with fluoro or methoxy;
e) $R^1$ is pyridinyl optionally substituted with fluoro;
f) $R^2$ is fluoro;
g) $R^2$ is chloro;
h) n is 0;
i) n is 1;
j) n is 2;

k) $R^3$ is hydrogen;
l) $R^3$ is methyl substituted with hydroxy;
m) $R^3$ is methyl;
n) $R^3$ is isopropyl substituted with hydroxy;
o) $R^4$ is hydrogen;
p) $R^4$ is methyl;
q) The compound of Formula I has an absolute configuration of (S) at the chiral center adjacent to the nitrogen of the aminothiazine ring;
r) The compound of Formula I is a free base;
s) The compound of Formula I is a pharmaceutically acceptable salt;
t) The compound of Formula I is the hydrochloride salt.
u) The compound of Formula I is the dihydrochloride salt.

A preferred embodiment of the present invention relates to compounds of Formula I, where $R^1$ is pyrimidinyl, pyridinyl optionally substituted one or two times at each instance independently selected from chloro, fluoro, or methoxy, or pyrazinyl optionally substituted with fluoro; $R^2$ is chloro or fluoro; $R^3$ is hydrogen, methyl, methyl substituted with hydroxy, or iso-propyl substituted with hydroxy; $R^4$ is hydrogen or methyl; and n is 0, 1 or 2; or a pharmaceutically acceptable salt thereof. In said embodiment, it is preferred that the absolute configuration of the chiral center adjacent to the nitrogen of the aminothiazine ring is (S); or a pharmaceutically acceptable salt thereof.

Another preferred embodiment of the present invention relates to compounds of Formula I where $R^1$ is pyrimidinyl, pyridinyl optionally substituted one or two times at each instance independently selected from chloro, fluoro, or methoxy, or pyrazinyl optionally substituted with fluoro; $R^2$ is chloro or fluoro; $R^3$ is hydrogen, methyl, methyl substituted with hydroxy, or iso-propyl substituted with hydroxy; $R^4$ is hydrogen; and n is 0, 1 or 2; or a pharmaceutically acceptable salt thereof. In said embodiment, it is preferred that the absolute configuration of the chiral center adjacent to the nitrogen of the aminothiazine ring is (S); or a pharmaceutically acceptable salt thereof.

A more preferred embodiment of the present invention relates to compounds of Formula I where $R^1$ is pyrimidinyl, pyridinyl optionally substituted one or two times at each instance independently selected from chloro or fluoro, or pyrazinyl optionally substituted with fluoro; $R^2$ is chloro or fluoro; $R^3$ is hydrogen, methyl; $R^4$ is hydrogen; and n is 0, 1 or 2; or a pharmaceutically acceptable salt thereof. In said embodiment, it is preferred that the absolute configuration of the chiral center adjacent to the nitrogen of the aminothiazine ring is (S); or a pharmaceutically acceptable salt thereof.

A further embodiment of the present invention relates to compounds of Formula I where $R^1$ is pyrimidinyl, pyridinyl optionally substituted with fluoro or methoxy, or pyrazinyl optionally substituted with fluoro; $R^2$ is fluoro; $R^3$ is hydrogen or methyl; $R^4$ is hydrogen; and n is 1 or 2; or a pharmaceutically acceptable salt thereof. In said embodiment, it is preferred that the absolute configuration of the chiral center adjacent to the nitrogen of the aminothiazine ring is (S); or a pharmaceutically acceptable salt thereof.

A most preferred embodiment of the present invention relates to compounds of Formula I where $R^1$ is pyrimidinyl, pyridinyl optionally substituted with fluoro, or pyrazinyl optionally substituted with fluoro; $R^2$ is fluoro; $R^3$ is hydrogen or methyl; $R^4$ is hydrogen; and n is 1 or 2; or a pharmaceutically acceptable salt thereof. In said embodiment, it is preferred that the absolute configuration of the chiral center adjacent to the nitrogen of the aminothiazine ring is (S), or a pharmaceutically acceptable salt thereof.

An especially preferred embodiment of the present invention relates to compounds of Formula I where $R^1$ is pyrimidinyl; $R^2$ is fluoro; $R^3$ is hydrogen; $R^4$ is hydrogen; and n is 2; or a pharmaceutically acceptable salt thereof. In said embodiment, it is preferred that the absolute configuration of the chiral center adjacent to the nitrogen of the aminothiazine ring is (S); or a pharmaceutically acceptable salt thereof.

A further especially preferred embodiment of the present invention relating to compounds of Formula I is

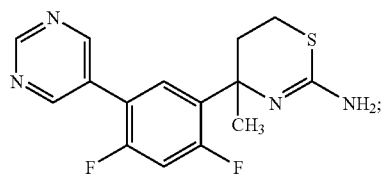

or a pharmaceutically acceptable salt thereof.

Another especially preferred embodiment of the present invention relating to compounds of Formula I is

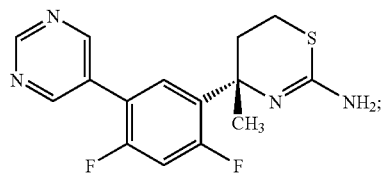

or a pharmaceutically acceptable salt thereof.

The compounds of Formula I are inhibitors of BACE. Thus, the present invention also provides a method of inhibiting BACE in a patient that comprises administering to a patient in need of said treatment a BACE-inhibiting amount of a compound of Formula I. It is preferred that the patient to be treated by the administration of the compounds of Formula I is human.

As inhibitors of BACE, the compounds of the present invention are useful for suppressing the production of Aβ peptide, and therefore for the treatment of disorders resulting from excessive Aβ peptide levels due to over-production and/or reduced clearance of Aβ peptide. A further embodiment of the present invention is the use of a compound of Formula I for the manufacture of a medicament for treating a disease or condition capable of being improved or prevented by inhibition of BACE. The compounds of Formula I are therefore believed to be useful in treating or preventing Alzheimer's disease, mild cognitive impairment, Down's Syndrome, Hereditary Cerebral Hemorrhage with Amyloidosis of the Dutch-Type, cerebral amyloid angiopathy, other degenerative dementias such as: dementias of mixed vascular and degenerative origin, dementia associated with Parkinson's disease, dementia associated with progressive supranuclear palsy, dementia associated cortical basal degeneration, and diffuse Lewy body type of Alzheimer's disease.

The compounds of the present invention may be prepared by a variety of procedures known in the art, some of which are illustrated in the Schemes below. It will be recognized by one of skill in the art that the individual steps in the following schemes may be varied to provide the compounds of Formula I. The particular order of steps required to produce the compounds of Formula I is dependent upon the particular compound being synthesized, the starting compound, and the relative lability of the substituted moieties. The products of each step in the schemes below can be recovered by conventional methods, including extraction, evaporation, precipitation, chromatography, filtration, trituration, and crystallization.

Certain stereochemical centers have been left unspecified and certain substituents have been eliminated in the following schemes for the sake of clarity and are not intended to limit the teaching of the schemes in any way. Furthermore, individual isomers, enantiomers, or diastereomers may be separated at any convenient point in the synthesis of compounds of Formula I by methods such as chiral chromatography.

Additionally, the intermediates described in the following schemes contain a number of nitrogen protecting groups. The variable protecting group may be the same or different in each occurrence depending on the particular reaction conditions and the particular transformations to be performed. The protection and deprotection conditions are well known to the skilled artisan and are described in the literature. See. e.g., Greene and Wuts, *Protective Groups in Organic Synthesis*, supra.

In the schemes below, all substituents, unless otherwise indicated, are previously defined. As will be appreciated, compounds of formulae (1a) to (1e), (2), and (3) can be readily prepared by methods that are well-known and established in the art, including methods and procedures similar to those described herein. The requisite starting materials are either commercially available or may be prepared from commercially available materials by methods well known to the skilled artisan.

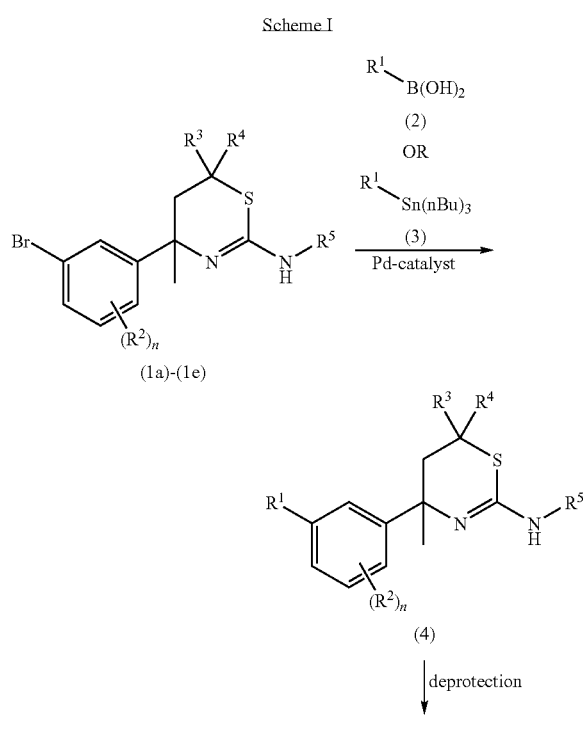

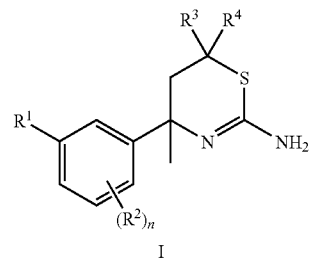

Scheme I depicts the reaction of an appropriate compound of any of formulae (1a) to (1e), where $R^5$ is a nitrogen protecting group, such as acetyl, benzoyl, or t-butoxycarbonyl, with an appropriate compound of formula (2) or formula (3) to give a compound of Formula I after the deprotection of the intermediate (4).

A compound of any of formulae (1a) to (1e) is reacted with a compound of formula (2) in a Suzuki coupling reaction using a suitable palladium reagent, such as bis(triphenylphoshine)palladium(II) chloride, palladium tetrakistriphenylphosphine, $PdCl_2$, or palladium(II) acetate, in the presence of a suitable base, such as cesium carbonate, sodium carbonate, or potassium carbonate. Such reactions are carried out in a suitable solvent, such as 1,2-dimethoxyethane, water, ethanol, acetonitrile, dimethylformamide, or dioxane, or mixtures thereof.

Alternatively, a compound of any of formulae (1a) to (1e) is reacted with a compound of formula (3) in a Stille coupling reaction using a suitable palladium reagent, such as bis(triphenylphoshine)palladium(II) chloride, $PdCl_2$, or palladium tetrakistriphenylphosphine, in the presence of a suitable additive, such as lithium chloride or cesium fluoride. Such reactions are carried out in a suitable solvent, such as toluene or DMF, or mixtures thereof.

In an optional step, a pharmaceutically acceptable salt of a compound of Formula I can be formed by reacting an appropriate free base of Formula I with an appropriate pharmaceutically acceptable acid in a suitable solvent under standard conditions. Additionally, the formation of such salts can occur simultaneously upon deprotection of a nitrogen protecting group. The formation of such salts is well known and appreciated in the art.

Compounds of formula (1a) can be prepared by two variants. Schemes II and III depict the synthetic steps starting with an appropriate compound of formula (i) to give a compound of formula (1a) in which $R^6$ is methyl or ethyl and $R^5$ is a suitable nitrogen protecting group, such as acetyl, benzoyl, or t-butoxycarbonyl.

Scheme II

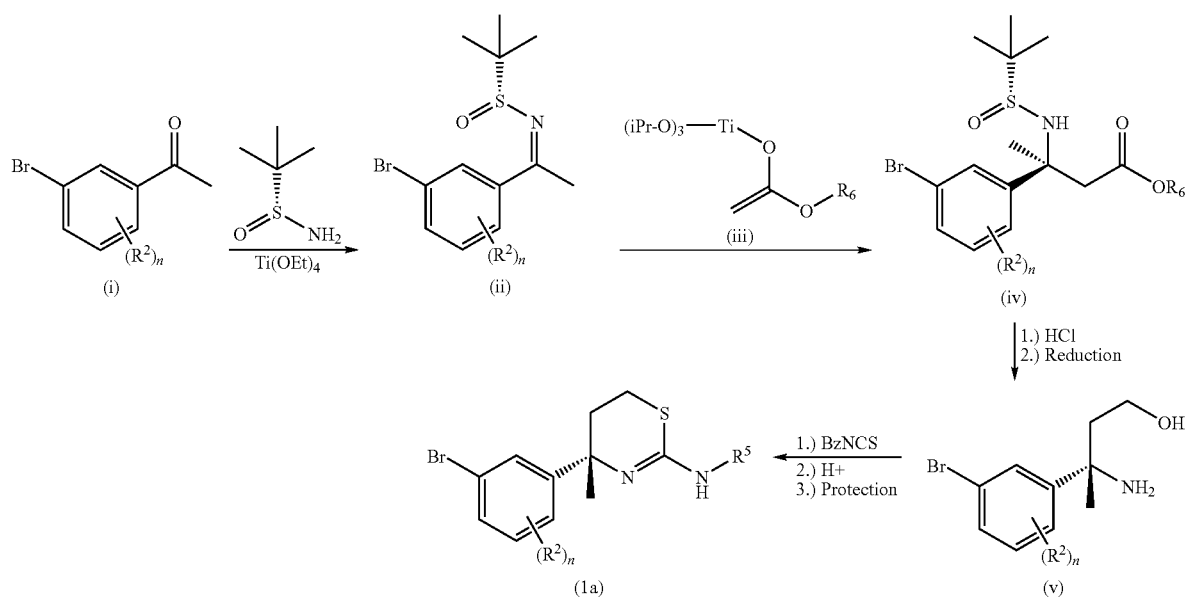

In Scheme II, a compound of formula (i) is reacted with 2-methyl-propane-2-sulfinic acid amide in the presence of Ti(OEt)$_4$ in a suitable solvent, such as THF, to give a compound of formula (ii). A compound of formula (iii) is prepared by adding n-BuLi to diisopropylamine in a suitable solvent, such as THF. The appropriate acetate compound is added followed by an excess of chlorotitanium triisopropoxide. A compound of formula (ii) is added to the solution of a compound of formula (iii) to give a compound of formula (iv). The deprotection of the amine is carried out by methods known in the art and is followed by the reduction of the ester to the alcohol by methods well known in the art, for example by the use of lithium aluminum hydride or lithium borohydride. To the alcohol (v) is added benzoyl isothiocyanate. The intermediate compound is treated with HCl to facilitate both thiazene formation and removal of the benzoyl group, and then a suitable nitrogen protecting group is added to give a compound of the formula (1a).

Scheme III

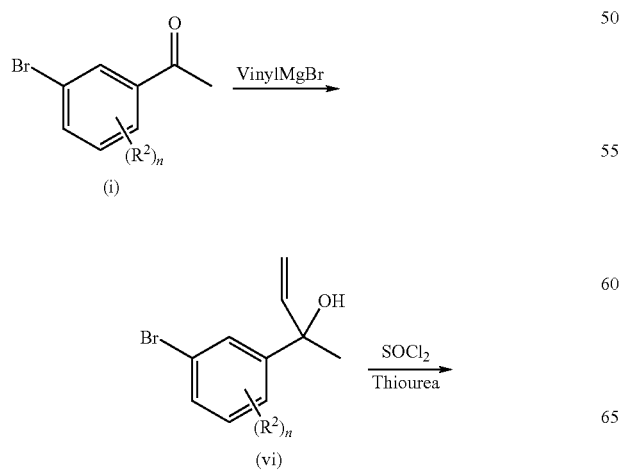

-continued

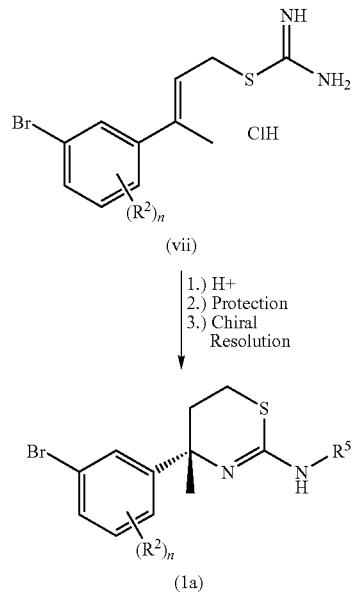

In Scheme III, an excess of vinylmagnesium bromide is added to a compound of formula (i) in a suitable solvent, such as THF, to give a compound of formula (vi). The alcohol (vi) is treated with thionyl chloride or PBr$_3$ in a suitable solvent, such as hexane or ethanol, followed by the addition of thiourea to give a compound of formula (vii). The compound of formula (vii) is treated with acid at an elevated temperature to provide the racemic aminothiazine which is protected with a suitable nitrogen protecting group and subjected to purification conditions, such as chiral chromatography or crystallization, to give a compound of formula (1a).

Scheme IV

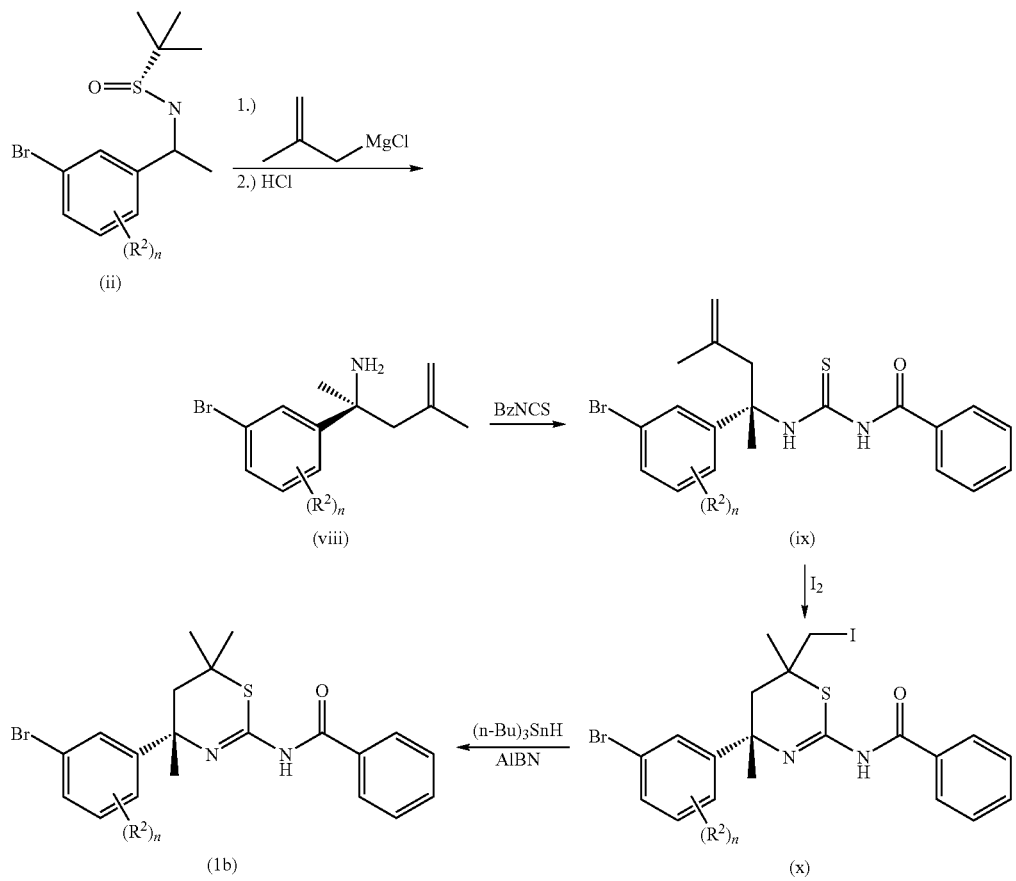

Scheme IV depicts the synthetic steps starting with an appropriate compound of formula (ii) to give a compound of formula (1b). An excess of 2-methylallylmagnesium chloride is added to a solution of a compound of formula (ii) in a suitable solvent, such as dichloromethane. The resulting intermediate is treated with a solution of HCl in a suitable solvent, such as dioxane, to give a compound of formula (viii). The amine (viii) is reacted with benzoyl isothiocyanate in a suitable solvent, such as THF, to give a compound of formula (ix). Treatment of a compound of formula (ix) with an excess of iodine in a suitable solvent, such as dichloromethane, will give a compound of formula (x). Finally, addition of tri-n-butyltin hydride and AIBN in a suitable solvent, such as toluene, will give a compound of formula (1b).

Scheme V

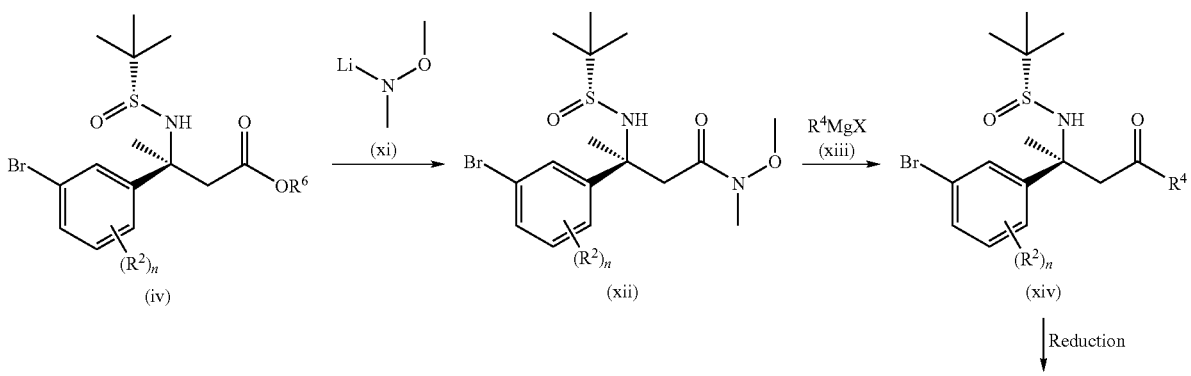

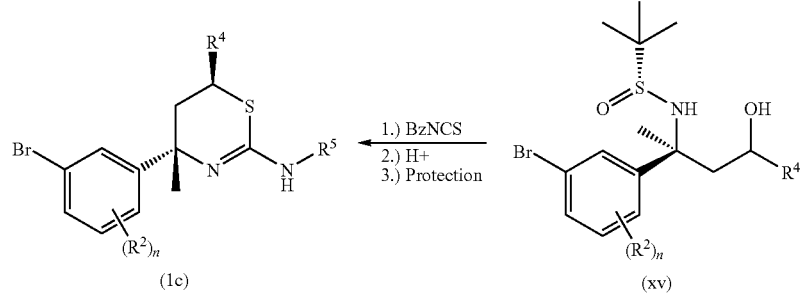

Scheme V depicts the synthetic steps to give a compound of formula (1c) starting with an appropriate compound of formula (iv). X is bromo or chloro. $R^5$ is a suitable nitrogen protecting group. $R^6$ is methyl or ethyl. Compound (xi) is prepared by reacting N,O-dimethylhydroxylamine with an excess of butyl lithium in a suitable solvent, such as THF. A compound of formula (iv) is added to a solution of the compound (xi) to give a compound of formula (xii). An excess of the appropriate magnesium halide (xiii) is added to a solution of a compound of formula (xii) in a suitable solvent, such as THF. The resulting ketone (xiv) is reduced to the alcohol (xv) by conditions well known and appreciate in the art, for example by sodium borohydride in a suitable solvent, such as methanol. To the alcohol (xv) is added benzoyl isothiocyanate. The intermediate compound is treated with HCl and then a suitable nitrogen protecting group is added to give a compound of the formula (1c).

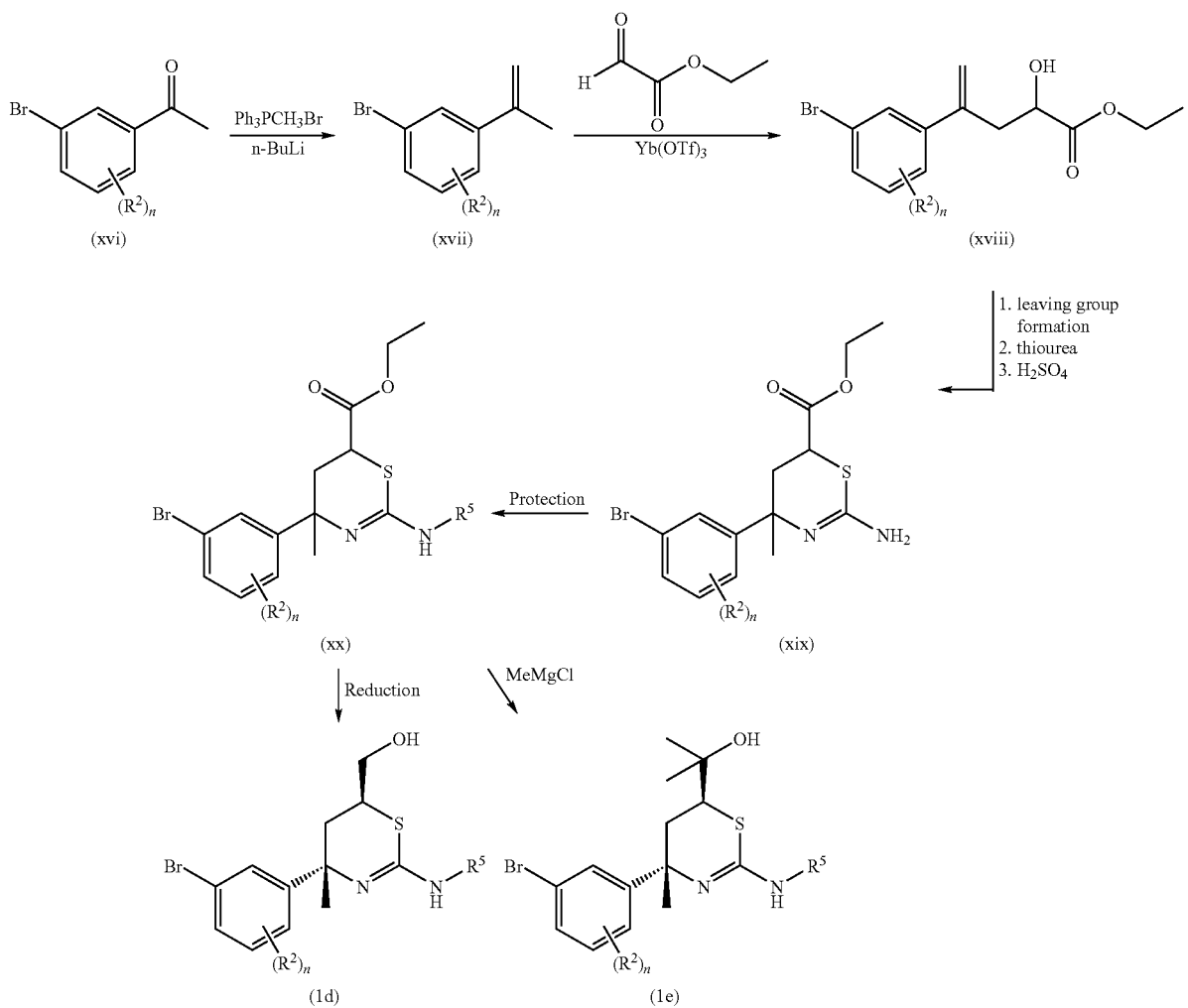

Scheme VI depicts the synthetic steps to give a compound of formula (1d) and a compound of formula (1 e), starting with an appropriate compound of formula (xvi), where $R^5$ is a suitable nitrogen protecting group.

A compound of formula (xvii) is prepared by first reacting (methyl)triphenylphosphonium bromide and n-butyl lithium in a suitable solvent, such as THF. To this solution, a compound of formula (xvi) is added slowly, for instance by an addition funnel or syringe pump. A compound of formula (xviii) is prepared by the addition of ethyl glyoxalate and ytterbium trifluoromethanesulfonate to a compound of formula (xvii) in a suitable solvent, such as acetonitrile.

A compound of formula (xix) is prepared via a three step process: first, the alcohol of a compound of formula (xviii) is transformed to a leaving group, for example by reaction with trifluoromethanesulfonic acid anhydride in the presence of an appropriate amine base, such as 2,6-lutidine or diisopropylethyl amine in a suitable solvent such as methylene chloride. An excess of thiourea is added and then the resulting intermediate is added to an excess of sulfuric acid. The resulting amino group of a compound of formula (xix) is protected with a suitable nitrogen protecting group by methods well known and described in the art to give a compound of formula (xx). The reaction of a compound of formula (xx) can be carried out in two variants to yield either a compound of formula (1d) or a compound of formula (1 e).

A compound of (1d) can be prepared by the reduction of the ester of compound (xx) by methods well known or described in the art, for example, an excess of lithium borohydride in a suitable solvent, such as THF.

A compound of (1e) can be prepared by reacting a compound of formula (xx) with an excess of methylmagnesium chloride in a suitable solvent, such as THF.

PREPARATIONS AND EXAMPLES

The following preparations and examples further illustrate the invention.

The names for the compounds of the present invention are provided by ChemDraw® Ultra, version 10.0.

The abbreviations used herein are defined according to *Aldrichimica Acta*, Vol. 17, No. 1, 1984. Other abbreviations are defined as follows: "SCX" is strong cation exchange; "ca." is about or approximately; "EtOAc" is ethyl acetate; "MeOH" is methanol; "DCM" is dichloromethane; "THF" is tetrahydrofuran; "Et$_2$O" is diethyl ether; "(OEt)" is ethoxide; "equiv" is equivalents; "FRET" is fluorescence resonance energy transfer; "RFU" is relative fluorescence unit; "DMEM" is Dulbecco's Modified Eagle's Medium; "F12" is Ham's F12 medium; "FBS" is Fetal Bovine Sera.

The mass spectrometry data, unless specified otherwise, is obtained via LC/MS: Xbridge C18 (2.1×50 μm×3.5 μm) column at a temperature of 50° C.+/−10° C. with a flow rate of 1 mL/min. The elution system is 5 to 100% ACN w/10 mM ammonium bicarbonate (pH 10) for 7.0 minutes then held at 100% ACN for 1.0 minute coupled with electrospray ionization (100-800 amu scan range; 0.2 amu step; 80v Fragmentor; 1.0 gain; 80 threshold).

Certain compounds are purified via HPLC, method A: Xterra® RP18 (30×300 mm) column at ambient temperature with a flow rate of 40 mL/min. The elution system is or consists of an isocratic gradient of 0:100 (acetonitrile: (0.1% HCl in H$_2$O)) for 1-5 minutes followed by a linear gradient from 0:100 (acetonitrile: (0.1% HCl in H$_2$O)) to 50:50 (acetonitrile: (0.1% HCl in H$_2$O)) over 20 minutes. Any other HPLC conditions are otherwise specified.

Preparation 1

(R)-2-Methyl-propane-2-sulfinic acid [1-(5-bromo-2,4-difluoro-phenyl)-ethylidene]-amide

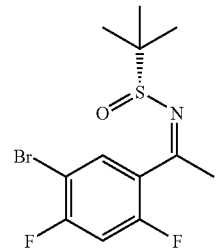

To a solution of 1-(5-bromo-2,4-difluoro-phenyl)-ethanone (19 g, 64.7 mmoles, 1 equiv.) and (R)-2-methyl-propane-2-sulfinic acid amide (10.2 g, 84.1 mmoles, 0.76 equiv) in THF (0.3 M, 215 mL) is added Ti(OEt)$_4$ (29.5 g, 129 mmoles, 2.0 equiv) in a single portion at ambient temperature. The reaction is heated to 70° C. and allowed to stir 18 h. The reaction is cooled to ambient temperature, and poured into water. The resulting suspension is filtered through a pad of diatomaceous earth and washed with ethyl acetate. The filtrate is collected and extracted with ethyl acetate. The organic layers are combined, dried over sodium sulfate, filtered, and concentrated under reduced pressure to give a residue. The residue is purified by silica gel chromatography, eluting with a linear gradient of hexane to hexane:ethyl acetate (3:1) over 20 minutes to give the title compound (81% yield): MS (m/z): 338, 340 (M+1).

The following compounds in Table 1 are prepared essentially as described in the preparation of (R)-2-methyl-propane-2-sulfinic acid [1-(5-bromo-2,4-difluoro-phenyl)-ethylidene]-amide.

TABLE 1

| Prep. No. | Chemical name | Physical data MS (m/z) |
|---|---|---|
| 1a | (R)-2-Methyl-propane-2-sulfinic acid [1-(3-bromo-4-fluoro-phenyl)-ethylidene]-amide | 320, 322 (M + 1) |
| 1b | (R)-2-Methyl-propane-2-sulfinic acid [1-(5-bromo-2-fluoro-phenyl)-ethylidene]-amide | 320, 322 (M + 1) |
| 1c | (R)-N-(1-(3-bromophenyl)ethylidene)-2-methylpropane-2-sulfinamide | 302, 304 (M + 1) |
| 1d | (R)-N-(1-(5-bromo-2-chlorophenyl)ethylidene)-2-methylpropane-2-sulfinamide | 336, 338 (M + 1) |

Preparation 2

(S)-3-((R)-2-Methyl-propane-2-sulfinylamino)-3-(5-bromo-2,4-difluoro-phenyl)-butyric Acid Methyl Ester

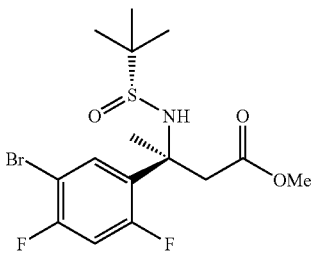

n-Butyl lithium (41.9 mL, 105 mmoles, 2 equiv) (2.5 M in Hexane) is added to a −78° C. solution of diisopropylamine (10.6 g, 105 mmoles, 2 equiv) in THF (262 mL). After 15 minutes, methyl acetate (7.7 g, 105 mmoles, 2 equiv) is added dropwise and the reaction is allowed to stir for 30 minutes. To the reaction is added dropwise a solution of chlorotitanium triisopropoxide (31.6 g, 115 mmoles, 2.2 equiv) in THF (50 mL). After stirring 60 minutes at −78° C., a solution of 2-methyl-propane-2-sulfinic acid [1-(3-bromo-phenyl)-ethylidene]-amide (12.2 g, 40.4 mmoles, 1 equiv) in THF (50 mL) is added dropwise. The reaction is stirred for 3 h at −78° C. The reaction is quenched with a saturated solution of ammonium chloride (100 mL), warmed to ambient temperature, and diluted with water (100 mL). The resulting suspension is filtered through a pad of diatomaceous earth and washed with ethyl acetate. The filtrate is collected and extracted with ethyl acetate. The organic layers are combined and dried over sodium sulfate, filtered, and concentrated under reduced pressure to give a residue. The residue is purified by silica gel chromatography eluting with a linear gradient of hexane:ethyl acetate (5:1) to hexane:ethyl acetate (10:7) over 20 minutes to give the title compound (72% yield): MS (m/z): 412, 414 (M+1).

The following compounds in Table 2 are prepared essentially as described in the preparation of (S)-3-((R)-2-methyl-propane-2-sulfinylamino)-3-(5-bromo-2,4-difluoro-phenyl)-butyric acid methyl ester.

TABLE 2

| Prep. No. | Chemical name | Physical data MS (m/z) |
|---|---|---|
| 2a | (S)-ethyl-3-(5-bromo-2,4-difluorophenyl)-3-((R)-1,1-dimethylethylsulfinamido)butanoate | 426, 428 (M + 1) |
| 2b | (S)-3-((R)-2-Methyl-propane-2-sulfinylamino)-3-(3-bromo-4-fluoro-phenyl)-butyric acid methyl ester | 394, 396 (M + 1) |
| 2c | S)-3-((R)-2-Methyl-propane-2-sulfinylamino)-3-(5-bromo-2-fluoro-phenyl)-butyric acid methyl ester | 394, 396 (M + 1) |
| 2d | (S)-3-((R)-2-Methyl-propane-2-sulfinylamino)-3-phenyl-butyric acid methyl ester | 376 378 (M + 1) |
| 2e | (S)-methyl 3-(5-bromo-2-chlorophenyl)-3-((R)-1,1-dimethylethylsulfinamido)butanoate | 410, 412 (M + 1) |

Preparation 3

(S)-methyl 3-amino-3-(2,4-difluorophenyl)-butanoate Hydrochloride

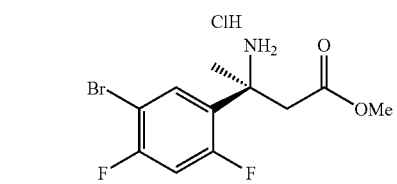

To a solution of (S)-3-((R)-2-methyl-propane-2-sulfinylamino)-3-phenyl-butyric acid methyl ester (15.5 g; 37.6 mmoles; 1 equiv) and methanol (100 mL) is added hydrogen chloride (4M in Dioxane) (100 mL, 400 mmol, 11 equiv) in a single portion. The reaction is stirred at room temperature for 1 h. The solvent removed under reduced pressure to give the title compound which is used without further purification (>95% yield): MS (m/z): 306, 308 (M+1).

The following compounds in Table 3 are prepared essentially as described in the preparation of (S)-methyl 3-amino-3-(2,4-difluorophenyl)-butanoate hydrochloride.

TABLE 3

| Prep. No. | Chemical name | Physical data MS (m/z) |
|---|---|---|
| 3a | (S)-methyl 3-amino-3-(3-bromo-4-fluorophenyl)-butanoate hydrochloride | 290, 292 (M + 1) |
| 3b | (S)-methyl 3-amino-3-(5-bromo-2-fluorophenyl)-butanoate hydrochloride | 290, 292 (M + 1) |
| 3c | (S)-methyl 3-amino-3-(4-fluorophenyl)-butanoate hydrochloride | 272, 274 (M + 1) |
| 3d | (S)-methyl 3-amino-3-(5-bromo-2-chlorophenyl)butanoate hydrochloride | 306, 308 (M + 1) |
| 3e | (S)-Ethyl-3-amino-3-(2,4-difluorophenyl)-butanoate hydrochloride | 322, 324 (M + 1) |

Preparation 4

(S)-3-amino-3-(5-bromo-2,4-difluorophenyl)butan-1-ol

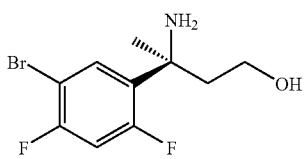

To a 0° C. solution of (S)-ethyl-3-amino-3-(2,4-difluorophenyl)-butanoate hydrochloride (40.2 g, 90.5 mmoles, 1 equiv) in THF (180 mL) is added lithium aluminum hydride (1 M in THF) (118 mL, 118 mmoles) over 45 minutes while maintaining the internal reaction temperature below 15° C. The reaction mixture is allowed to warm to ambient temperature and stir for 1.5 h. The reaction is cooled to 0° C. and quenched by the dropwise addition of water (4.5 mL), 2 M sodium hydroxide (4.5 mL), and water (13.6 mL). The resulting solid is removed by filtration and rinsed with ethyl acetate.

The filtrate is dried over MgSO$_4$ and filtered. The solvent is removed under reduced pressure to give the title compound which is used without further purification (71% yield, 73% purity as determined by LCMS): MS (m/z): 280, 282

Preparation 5

(S)-3-Amino-3-(3-bromo-phenyl)-butan-1-ol

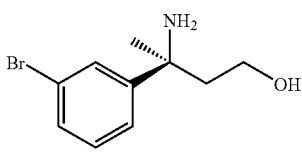

To a 0° C. solution of (S)-methyl 3-amino-3-(4-fluorophenyl)-butanoate hydrochloride (14 g, 38.6 mmoles, 1 equiv]) in THF (200 mL) is added lithium borohydride (1.67 g, 77.1 mmoles, 2 equiv) carefully. After 5 minutes, the reaction mixture is heated to 50° C. and stirred. Upon completion, the reaction is cooled in an ice bath and quenched by dropwise addition of water. The reaction is acidified with 1 N HCl (100 mL). After stirring for 1 h, the solution is made basic with 5N NaOH, and extracted with dichloromethane. The organic layers are combined, dried over sodium sulfate, filtered, and concentrated under reduced pressure to give the title compound (94% yield): MS (m/z): 244.0 and 246.0 (M+1).

The following compounds in Table 4 are prepared essentially according to the preparation of (S)-3-Amino-3-(3-bromo-phenyl)-butan-1-ol.

TABLE 4

| Prep. No. | Chemical name | Physical data MS (m/z) |
|---|---|---|
| 5a | (S)-3-amino-3-(3-bromo-4-fluorophenyl)butan-1-ol | 262, 264 (M + 1) |
| 5b | (S)-3-amino-3-(5-bromo-2-fluorophenyl)butan-1-ol | 262, 264 (M + 1) |
| 5c | (S)-3-amino-3-(5-bromo-2-chlorophenyl)butan-1-ol | 278, 280 (M + 1) |

Preparation 6

(S)-1-Benzoyl-3-[1-(5-bromo-2,4-difluoro-phenyl)-3-hydroxy-1-methyl-propyl]-thiourea

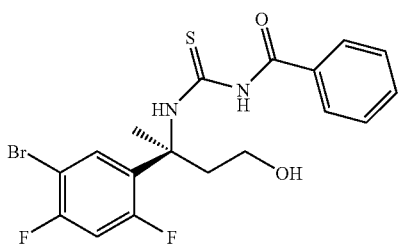

To a solution of (S)-3-amino-3-(5-bromo-2,4-difluorophenyl)-butan-1-ol (9.5 g, 34 mmoles, 1 equiv) in THF (50 mL) is added bis(trimethylsilyl)trifluoroacetamide (8.7 g, 34 mmol, 1 equiv). After 2 h, benzoyl isothiocyanate (5.5 g, 34 mmoles, 1 equiv) is added dropwise. The reaction is stirred 18 h, quenched with water, and extracted with ethyl acetate. The combined organic phases are extracted with 1 N HCl and saturated aqueous NaCl. The organic phase is dried over sodium sulfate, filtered, and concentrated under reduced pressure to give the title compound (>95% yield, 90% purity as determined by LCMS): MS (m/z): 443, 445 (M+1).

The following compounds in Table 5 are prepared essentially as described in the preparation of (S)-1-benzoyl-3-[1-(5-bromo-2,4-difluoro-phenyl)-3-hydroxy-1-methyl-propyl]-thiourea.

TABLE 5

| Prep. No. | Chemical name | Physical data MS (m/z) |
|---|---|---|
| 6a | (S)-1-Benzoyl-3-[1-(3-bromo-4-fluoro-phenyl)-3-hydroxy-1-methyl-propyl]-thiourea | 425, 427 (M + 1) |
| 6b | (S)-1-Benzoyl-3-[1-(5-bromo-2-fluoro-phenyl)-3-hydroxy-1-methyl-propyl]-thiourea | 425, 427 (M + 1) |
| 6c | (S)-N-(2-(3-bromophenyl)-4-hydroxybutan-2-ylcarbamothioyl)pivalamide | 359, 361 (M + 1) |
| 6d | (S)-N-(2-(5-bromo-2-chlorophenyl)-4-hydroxybutan-2-ylcarbamothioyl)benzamide | 441, 443 (M + 1) |

Preparation 7

(S)-4-(5-bromo-2,4-difluorophenyl)-4-methyl-5,6-dihydro-4H-1,3-thiazin-2-amine

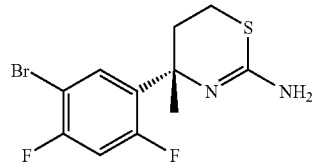

To a solution of (S)-1-benzoyl-3-[1-(5-bromo-2,4-difluoro-phenyl)-3-hydroxy-1-methyl-propyl]-thiourea (41 g, 68 mmoles) in 1,4-dioxane (20 mL) is added an aqueous solution of HCl (5 N, 407 mL, 2.0 moles, 30 equiv). The resulting suspension is warmed to 100° C. After stirring for 20 h, the reaction is concentrated under reduced pressure. The resulting mixture is treated with an aqueous solution of HCl (5 N, 407 mL, 2.0 moles) and stirred at 100° C. for 18 h. The suspension is cooled to 10° C. and the pH is adjusted to pH 10 with a 50% aqueous solution of NaOH. The resulting aqueous solution is extracted with ethyl acetate. The organic layers are combined, dried over sodium sulfate, filtered, and concentrated under reduced pressure. The residue is purified by silica gel flash column chromatography eluting with a step gradient of hexane:acetone (4:1) to hexane:acetone (3:1) to give the title compound (57% yield, 85% purity as determined by LCMS): MS (m/z): 321, 323 (M+1).

The following compounds in Table 6 are prepared essentially according to the preparation of (S)-4-(5-bromo-2,4-difluorophenyl)-4-methyl-5,6-dihydro-4H-1,3-thiazin-2-amine.

TABLE 6

| Prep. No. | Chemical name | Physical data MS (m/z) |
|---|---|---|
| 7a | (S)-4-(3-Bromo-4-fluoro-phenyl)-4-methyl-5,6-dihydro-4H-[1,3]thiazin-2-ylamine hydrochloride | 303, 305 (M + 1) |
| 7b | (S)-4-(3-bromophenyl)-4-methyl-5,6-dihydro-4H-1,3-thiazin-2-amine hydrochloride | 285, 287 (M + 1) |
| 7c | (S)-4-(5-bromo-2-chlorophenyl)-4-methyl-5,6-dihydro-4H-1,3-thiazin-2-amine | 319, 321 (M + 1) |

Preparation 8

(S)-[4-(5-Bromo-2-fluoro-phenyl)-4-methyl-5,6-dihydro-4H-[1,3]thiazin-2-yl]-carbamic Acid Tert-Butyl Ester A solution of (S)-1-benzoyl-3-[1-(5-bromo-2-fluoro-phenyl)-3-hydroxy-1-methyl-propyl]-thiourea (0.79 g, 1.8 mmoles) and aqueous HCl (5 N, 25 mL, 71 mmoles) is warmed to 100° C. After stirring for 6 h, the reaction is cooled to ambient temperature and allowed to stand overnight. The reaction is concentrated under reduced pressure to give crude (S)-4-(5-bromo-2-fluorophenyl)-4-methyl-5,6-dihydro-4H-1,3-thiazin-2-amine hydrochloride [MS (m/z): 303, 305 (M+1)].

To a solution of (S)-4-(5-bromo-2-fluorophenyl)-4-methyl-5,6-dihydro-4H-1,3-thiazin-2-amine hydrochloride in THF (30 mL) and saturated aqueous sodium bicarbonate (15 mL) is added di-t-butyldicarbonate (0.77 g, 3.5 mmoles). After 4 h, the reaction is diluted with water, extracted with ethyl acetate, dried over sodium sulfate, filtered, and concentrated under reduced pressure. The residue is purified by silica gel flash column chromatography eluting with a linear gradient of hexane to hexane:ethyl acetate (3:1) to give the title compound (69% yield): MS (m/z): 403, 405 (M+1).

Preparation 9

(S)-tert-butyl 4-(5-bromo-2,4-difluorophenyl)-4-methyl-5,6-dihydro-4H-1,3-thiazin-2-ylcarbamate

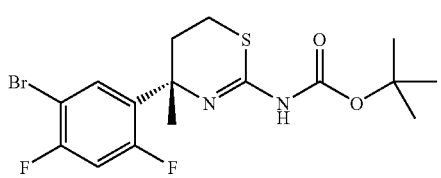

To a solution of (S)-4-(5-bromo-2,4-difluorophenyl)-4-methyl-5,6-dihydro-4H-1,3-thiazin-2-amine (14.3 g, 39 mmoles 1 equiv) in 1,4-dioxane (190 mL) is added a saturated aqueous solution of sodium bicarbonate (190 mL) and water (30 mL) at ambient temperature. The suspension is stirred for 5 minutes followed by the addition of di-tert-butyldicarbonate (17 g, 78 mmoles, 2 equiv). After 1 h, the reaction is diluted with water, extracted with ethyl acetate, dried over magnesium sulfate, filtered, and concentrated under reduced pressure. The residue is purified by silica gel chromatography eluting with hexane:ethyl acetate (4:1) to give the title compound (78% yield): MS (m/z): 421, 423 (M+1).

The following compounds in Table 7 are prepared essentially as described in the preparation of (S)-tert-butyl 4-(5-bromo-2,4-difluorophenyl)-4-methyl-5,6-dihydro-4H-1,3-thiazin-2-ylcarbamate.

TABLE 7

| Prep. No. | Chemical name | Physical data MS (m/z) |
|---|---|---|
| 9a | (S)-[4-(3-Bromo-4-fluoro-phenyl)-4-methyl-5,6-dihydro-4H-[1,3]thiazin-2-yl]-carbamic acid tert-butyl ester | 403, 405 (M + 1) |
| 9b | (S)-tert-butyl 4-(3-bromophenyl)-4-methyl-5,6-dihydro-4H-1,3-thiazin-2-ylcarbamate | 385, 387 (M + 1) |
| 9c | (S)-tert-butyl 4-(5-bromo-2-chlorophenyl)-4-methyl-5,6-dihydro-4H-1,3-thiazin-2-ylcarbamate | 419, 421 (M + 1) |

Preparation 10

2-Bromo-3-yl-but-3-en-2-ol

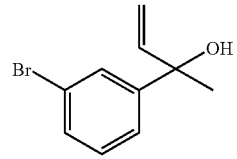

To a solution of 3-bromoacetophenone (50 g, 250 mmoles; 1 equiv) in MTBE (375 mL) at 10° C., is added vinylmagnesium bromide (0.7 M in THF, 250 mmoles; 360 mL, 1 equiv) dropwise. The reaction is heated to reflux for 16 h. The reaction is cooled and quenched with a saturated aqueous solution of ammonium chloride. The mixture is diluted with water, extracted with ethyl acetate, dried over magnesium sulfate, filtered, and concentrated under reduced pressure. The residue is purified by silica gel chromatography eluting with a step gradient of hexanes:ethyl acetate (9:1) to hexanes:ethyl acetate (4:1) to give the title compound (40 g, 42% yield): $^1$H NMR (400 MHz, CDCl$_3$): 1.64 (s, 3H), 5.18 (d, J=14 Hz, 1H), 5.30 (d, J=23 Hz, 1H), 6.13 (dd, J=14, 23 Hz, 1H), 7.21 (t, J=11 Hz, 1H), 7.36-7.40 (m, 2H), 7.63 (s, 1H).

Preparation 11

2-[3-(3-Bromo-phenyl)-but-2-enyl]-isothiourea Hydrochloride

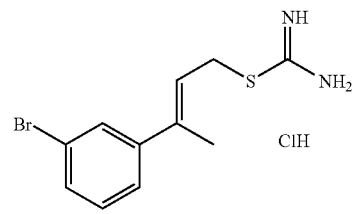

To a 0° C. solution of 2-bromo-3-yl-but-3-en-2-ol (11 g, 29 mmoles, 1 equiv) and hexane (20 mL) is added thionyl chloride (6.9 g, 58 mmoles, 2 equiv). The reaction is allowed to warm to ambient temperature at which time gas vigorously evolves. The reaction is stirred at ambient temperature until the gas ceases to evolve and the solvent is removed under reduced pressure. The resulting residue is dissolved in acetonitrile (100 mL). Thiourea (2.2 g, 29 mmoles, 1 equiv) is added and the reaction is heated to 50° C. After 2 h, the reaction is cooled to ambient temperature. The resulting precipitate is collected by filtration and washed with acetonitrile to give the title compound (90% yield): MS (m/z): 285.0, 287.0 (M+1).

Preparation 12

4-(3-Bromo-phenyl)-4-methyl-5,6-dihydro-4H-[1,3]thiazin-2-ylamine

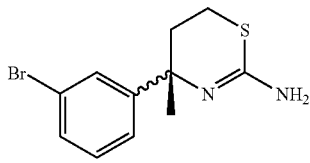

A suspension of 2-[3-(3-bromo-phenyl)-but-2-enyl]-isothiourea hydrochloride (17 g, 52 mmoles) in 12 M HCl (53 mL, 640 mmoles, 12 equiv) is heated to 100° C. After 24 h, the solution is cooled to ambient temperature. The pH of the solution is adjusted to pH 10 with aqueous 2N NaOH and extracted with ethyl acetate. The organic layers are combined, dried over magnesium sulfate, filtered, and concentrated under reduced pressure to give the title compound (70% yield): MS (m/z): 285.0, 287.0 (M+1).

Preparation 13

N-(4-(3-bromophenyl)-4-methyl-5,6-dihydro-4H-1,3-thiazin-2-yl)acetamide

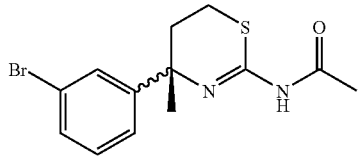

To a 0° C. solution of 4-(3-bromo-phenyl)-4-methyl-5,6-dihydro-4H-[1,3]thiazin-2-ylamine (10 g, 35 mmoles, 1 equiv) and triethylamine (4.3 g, 42 mmoles, 1.2 equiv) in dichloromethane (70 mL) is added dropwise acetyl chloride (2.8 g, 35 mmoles, 1 equiv) over 5 minutes. The reaction is allowed to warm to ambient temperature. After 1 h, the reaction is diluted with dichloromethane and extracted with water. The organic layers are separated, dried over magnesium sulfate, filtered, and concentrated under reduced pressure. The resulting residue is purified by silica gel chromatography eluting with hexane:ethyl acetate (1:1) to give the title compound (87% yield): MS (m/z): 327, 329 (M+1).

Preparation 14

(S)-N-[4-(3-Bromo-phenyl)-4-methyl-5,6-dihydro-4H-[1,3]thiazin-2-yl]-acetamide 4-(3-bromo-phenyl)-4-methyl-5,6-dihydro-4H-[1,3]thiazin-2-ylamine (20 g, 61 mmole) is purified by HPLC chiral separation [Column: 8×32 cm chiralpak AD; Eluent: 60:40:0.2 (isopropyl alcohol: heptanes: dimethylethylamine); Flow: 350 mL/min at UV 260 nm]. The second eluting isomer is isolated to provide the enantiomerically enriched title compound (35% Yield): MS (m/z): 327, 329 (M+1)

Preparation 15

(S)-[4-(2,4-Difluoro-5-pyrimidin-5-yl-phenyl)-4-methyl-5,6-dihydro-4H-[1,3]thiazin-2-yl]-carbamic Acid Tert-Butyl Ester

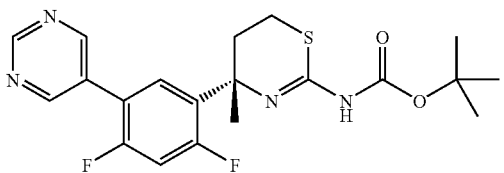

To a 100° C. solution of (S)-4-(5-bromo-2,4-difluorophenyl)-4-methyl-5,6-dihydro-4H-1,3-thiazin-2-amine (12.6 g, 29.9 mmol, 1 equiv) in 1,2-dimethoxyethane:water:ethanol (15:7:5, 300 mL) is added a pyrimidine-5-boronic acid (25 g, 203 mmoles, 6.8 equiv) followed by cesium carbonate (58 g, 180 mmoles, 6 equiv) and bis(triphenylphosphine)palladium (II) chloride (4.2 g, 6.0 moles, 0.2 equiv). After 40 minutes, the reaction is cooled to ambient temperature, diluted with water, and extracted with ethyl acetate. The organic phase is dried over magnesium sulfate, filtered, and concentrated under reduced pressure. The residue is purified by silica gel chromatography eluting with a step gradient of hexanes:ethyl acetate (7:3) to hexanes:ethyl acetate (1:1) to give the title compound (67% yield): MS (m/z): 421 (M+1).

The following compounds in Table 8 are prepared essentially as described in the preparation of (S)-[4-(2,4-difluoro-5-pyrimidin-5-yl-phenyl)-4-methyl-5,6-dihydro-4H-[1,3]thiazin-2-yl]-carbamic acid tert-butyl ester.

TABLE 8

| Prep. No. | Chemical name | Physical data MS (m/z) |
|---|---|---|
| 15a | (S)—N-{4-[3-(5-Methoxy-pyridin-3-yl)-phenyl]-4-methyl-5,6-dihydro-4H-[1,3]thiazin-2-yl}-acetamide | 356 (M + 1) |
| 15b | (S)—N-(4-(3-(5-chloro-2-fluoropyridin-3-yl)phenyl)-4-methyl-5,6-dihydro-4H-1,3-thiazin-2-yl)acetamide | 378 (M + 1) |
| 15c | (S)-[4-(4-Fluoro-3-pyrimidin-5-yl-phenyl)-4-methyl-5,6-dihydro-4H-[1,3]thiazin-2-yl]-carbamic acid tert-butyl ester | 403 (M + 1) |
| 15d | (S)-[4-(2-Fluoro-5-pyrimidin-5-yl-phenyl)-4-methyl-5,6-dihydro-4H-[1,3]thiazin-2-yl]-carbamic acid tert-butyl ester | 403 (M + 1) |
| 15e | (S)—N-[4-Methyl-4-(3-pyrimidin-5-yl-phenyl)-5,6-dihydro-4H-[1,3]thiazin-2-yl]-acetamide | 327 (M + 1) |
| 15f | (S)-{4-[4-Fluoro-3-(2-fluoro-pyridin-3-yl)-phenyl]-4-methyl-5,6-dihydro-4H-[1,3]thiazin-2-yl}-carbamic acid tert-butyl ester | 420 (M + 1) |
| 15g | (S)-{4-[2,4-Difluoro-5-(2-fluoro-pyridin-3-yl)-phenyl]-4-methyl-5,6-dihydro-4H-[1,3]thiazin-2-yl}-carbamic acid tert-butyl ester | 438 (M + 1) |
| 15h | (S)-tert-butyl 4-(2,4-difluoro-5-(5-fluoropyridin-3-yl)phenyl)-4-methyl-5,6-dihydro-4H-1,3-thiazin-2-ylcarbamate | 438 (M + 1) |
| 15i | (S)-4-(2-chloro-5-(5-chloro-2-fluoropyridin-3-yl)phenyl)-4-methyl-5,6-dihydro-4H-1,3-thiazin-2-amine[1] | 370, 372 (M + 1) |
| 15j | N-{4-[3-(5-Methoxy-pyridin-3-yl)-phenyl]-4-methyl-5,6-dihydro-4H-[1,3]thiazin-2-yl}-acetamide | 356 (M + 1) |
| 15k | (S)—N-(4-(3-(2-fluoropyridin-3-yl)phenyl)-4-methyl-5,6-dihydro-4H-1,3-thiazin-2-yl)acetamide | 344 (M + 1) |

[1]The t-butoxycarbonyl group was cleaved under reaction conditions.

Preparation 16

(S)-4-(3-(2-fluoropyridin-3-yl)phenyl)-4-methyl-5,6-dihydro-4H-1,3-thiazin-2-amine

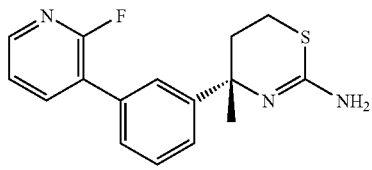

To a solution of (S)-N-(4-(3-(2-fluoropyridin-3-yl)phenyl)-4-methyl-5,6-dihydro-4H-1,3-thiazin-2-yl)acetamide (450 mg, 1.3 mmoles) in methanol (40 mL) is added a solution of $K_2CO_3$ (210 mg, 1.5 mmoles) in methanol:water (2:1, 15 mL). The reaction is stirred at room temperature for 6 h. The solvent is removed under reduced pressure and the residue is dissolved in ethyl acetate. The ethyl acetate layer is washed with water and saturated aqueous NaCl, dried over sodium sulfate, filtered and concentrated under reduced pressure to give a residue. The residue is purified by using SCX column chromatography to give the title compound (65% yield): MS (m/z): 302 (M+1).

Preparation 17

(S)-4-(3-bromo-4-fluorophenyl)-4-methyl-5,6-dihydro-4H-1,3-thiazin-2-amine

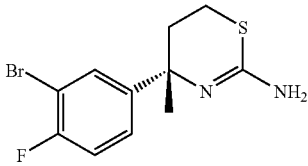

To a solution of (S)-tert-butyl 4-(3-bromo-4-fluorophenyl)-4-methyl-5,6-dihydro-4H-1,3-thiazin-2-ylcarbamate (1.1 g, 2.7 mmoles) and methanol (10 mL) is added trifluoroacetic acid (10 mL). The reaction mixture is warmed to 60° C. After 15 h, the solvent is removed under reduced pressure. Water is added to the resulting residue and the mixture is made basic with saturated sodium bicarbonate. The basic aqueous phase is extracted with dichloromethane. The organic phase is separated, dried over sodium sulfate, filtered, and the solvent removed under reduced pressure to give the title compound (62% yield): MS (m/z): 303, 305 (M+1).

Preparation 18

(S)-N-(4-(3-bromo-4-fluorophenyl)-4-methyl-5,6-dihydro-4H-1,3-thiazin-2-yl)acetamide To a solution of (S)-4-(3-bromo-4-fluorophenyl)-4-methyl-5,6-dihydro-4H-1,3-thiazin-2-amine (550 mg, 1.8 mmoles, 1.0 equiv) in tetrahydrofuran (20 mL) is added pyridine (720 mg, 9.0 mmoles, 5 equiv) and acetic acid anhydride (220 mg, 2.2 mmoles, 1.2 equiv). After 10 minutes, the reaction is poured into water and the aqueous mixture is extracted with dichloromethane. The organic phase is separated and washed with 1N HCl and saturated aqueous NaCl, dried over magnesium sulfate, filtered, and concentrated under reduced pressure to give the title compound (83% yield): MS (m/z) 345, 347 (M+1).

Preparation 19

(S)-tert-butyl 4-(4-fluoro-3-(pyrazin-2-yl)phenyl)-4-methyl-5,6-dihydro-4H-1,3-thiazin-2-ylcarbamate

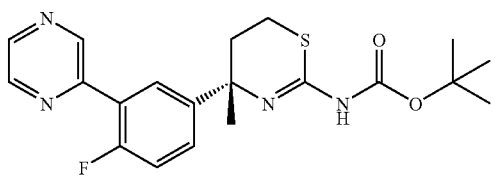

A solution of (S)-[4-(3-bromo-4-fluoro-phenyl)-4-methyl-5,6-dihydro-4H-[1,3]thiazin-2-yl]-carbamic acid tert-butyl ester (100 mg, 250 μmoles, 1 equiv), tetrakis(triphenylphosphine)palladium (14 mg, 12.40 μmoles, 0.05 equiv) and 2-tributylstannylpyrazine (96 mg, 250 μmoles, 1 equiv) in dioxane (3 mL) is irradiated in a laboratory-grade microwave to a temperature of 130° C. and held for 20 minutes. The solvent is removed under reduced pressure and the residue is purified by silica gel chromatography eluting with a linear gradient of hexane to hexane:ethyl acetate (1:4) ramp 20 min to give the title compound (14% yield, 90% purity as determined by LCMS): MS (m/z): 403 (M+1).

Preparation 20

(S)-N-(4-(4-fluoro-3-(3-fluoropyrazin-2-yl)phenyl)-4-methyl-5,6-dihydro-4H-1,3-thiazin-2-yl)acetamide To solution of (S)-N-(4-(3-bromo-4-fluorophenyl)-4-methyl-5,6-dihydro-4H-1,3-thiazin-2-yl)acetamide (500 mg, 1.5 mmoles, 1 equiv), 2-fluoro-3-(tributylstannyl)pyrazine (1.7 g, 4.3 mmoles, 3.0 equiv) in toluene (15 mL) is added bis(triphenylphosphine)palladium(II) chloride (51 mg, 72 μmoles, 0.05 equiv) and lithium chloride (92 mg, 2.2 mmoles, 1.5 equiv). The reaction is irradiated in a laboratory-grade microwave to a temperature of 130° C. and held for 3 h. The solvent is removed under reduced pressure and the residue is purified by silica gel chromatography eluting with a linear gradient of hexane to hexane:ethyl acetate (1:1) ramp 20 min to give the title compound (31% yield): MS (m/z): 363 (M+1).

The following compound in Table 9 is prepared essentially according to the preparation of (S)-N-(4-(4-fluoro-3-(3-fluoropyrazin-2-yl)phenyl)-4-methyl-5,6-dihydro-4H-1,3-thiazin-2-yl)acetamide.

TABLE 9

| Prep. No. | Chemical name | Physical data MS (m/z) |
|---|---|---|
| 20a | (S)—N-(4-(2,4-difluoro-5-(3-fluoropyrazin-2-yl)phenyl)-4-methyl-5,6-dihydro-4H-1,3-thiazin-2-yl)acetamide | 381 (M + 1) |

Preparation 21

(R)-N-((S)-2-(3-bromo-4-fluorophenyl)-4-methylpent-4-en-2-yl)-2-methylpropane-2-sulfinamide

KG2-E01905-021-2

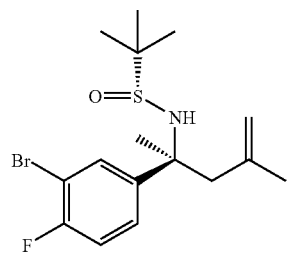

To a 0° C. solution of (R,Z)-N-(1-(3-bromo-4-fluorophenyl)ethylidene)-2-methylpropane-2-sulfinamide (10 g, 31 mmoles, 1.0 equiv) in dichloromethane (100 mL) is slowly added 2-methylallylmagnesium chloride (0.5 M in THF, 250 mL, 125.92 mmoles, 4 equiv). After 2 h, the reaction is quenched with saturated ammonium chloride and extracted with ethyl acetate. The solvent is removed under reduced pressure and the residue is purified by silica gel chromatography eluting with a linear gradient of dichloromethane to 10% dichloromethane:ethyl acetate to give the title compound (35% yield): MS (m/z): 376, 378 (M+1).

Preparation 22

(S)-2-(3-bromo-4-fluorophenyl)-4-methylpent-4-en-2-amine

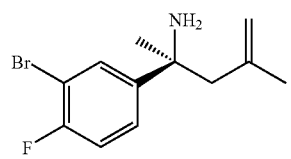

To a solution of (R)-N-((S)-2-(3-bromo-4-fluorophenyl)-4-methylpent-4-en-2-yl)-2-methylpropane-2-sulfinamide (1.8 g, 5.1 mmoles, 1 equiv) in 1,4-dioxane (6 mL) is added hydrogen chloride (4.0 M in 1,4-dioxane, 15 mL). The reaction is stirred for 5 minutes and the solvent is removed under reduced pressure. To the residue is added saturated aqueous sodium bicarbonate and the mixture is extracted with ethyl acetate. The combined organic phase is dried over sodium sulfate, filtered and concentrated under reduced pressure to give the title compound (97% yield): $^1$H NMR (CDCl$_3$, 400 MHz) δ 7.66 (dd, 1H, J=6.40, J=2.80 Hz), 7.37-7.33 (m, 1H), 7.02 (t, 1H, J=8.40 Hz), 4.83 (s, 1H), 4.62 (s, 1H), 2.47 (d, 1H, J=13.2 Hz), 2.35 (d, 1H, J=13.2 Hz), 1.44 (s, 3H), 1.36 (s, 3H).

Preparation 23

(S)-N-(2-(3-bromo-4-fluorophenyl)-4-methylpent-4-en-2-ylcarbamothioyl)benzamide

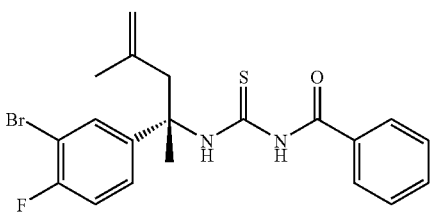

To a solution of (S)-2-(3-bromo-4-fluorophenyl)-4-methylpent-4-en-2-amine (1.3 g, 4.6 mmoles, 1.0 equiv) in THF (5 mL) is added benzoyl isothiocyanate (0.63 mL, 4.6 mmoles, 1 equiv). The reaction is stirred at room temperature for 3 h. The solvent is removed under reduced pressure and the residue is purified by silica gel chromatography eluting with a linear gradient of 20% dichloromethane: hexanes to 50% dichloromethane: hexanes to give the title compound (84% yield): MS (m/z): 457, 459 (M+23).

Preparation 24

N-((4S)-4-(3-bromo-4-fluorophenyl)-6-(iodomethyl)-4,6-dimethyl-5,6-dihydro-4H-1,3-thiazin-2-yl)benzamide

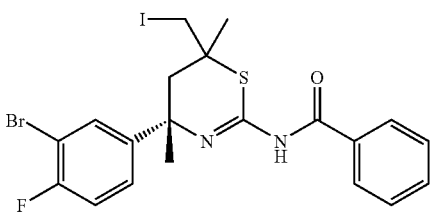

To a 0° C. solution of (S)-N-(2-(3-bromo-4-fluorophenyl)-4-methylpent-4-en-2-ylcarbamothioyl)benzamide (1.3 g, 3.0 mmoles, 1.0 equiv) in dichloromethane (40 mL) is added iodine (1.5 g, 5.9 mmoles, 2.0 equiv). The reaction is stirred at 0° C. for 1 h and gradually warmed to room temperature. The reaction mixture is quenched with saturated aqueous sodium thiosulfate. The aqueous layer is extracted with dichloromethane. The combined organic phase is dried over sodium sulfate, filtered and concentrated under reduced pressure to give the title compound (82% yield): MS (m/z): 561, 563 (M+1).

Preparation 25

(S)-N-(4-(3-bromo-4-fluorophenyl)-4,6,6-trimethyl-5,6-dihydro-4H-1,3-thiazin-2-yl)benzamide

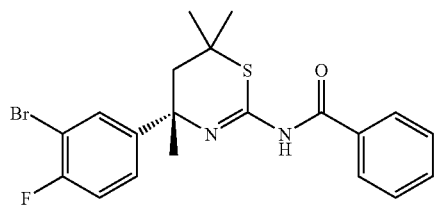

To a solution of N-((4S)-4-(3-bromo-4-fluorophenyl)-6-(iodomethyl)-4,6-dimethyl-5,6-dihydro-4H-1,3-thiazin-2-yl)benzamide (0.13 g, 0.23 mmoles, 1.0 equiv) in toluene (1.5 mL) is added 2-2'-azo-bis-isobutyronitrile (0.006 g, 0.03 mmoles, 0.15 equiv) and tri-n-butyltin hydride. The reaction mixture is stirred at room temperature for 3 h and concentrated under reduced pressure. The solvent is removed under reduced pressure and the residue is purified by silica gel chromatography eluting with a linear gradient of 5% ethyl acetate:hexanes to 20% ethyl acetate:hexanes to give the title compound (25% yield): MS (m/z): 435, 437 (M+1).

Preparation 26

(S)-N-(4-(4-fluoro-3-(pyrimidin-5-yl)phenyl)-4,6,6-trimethyl-5,6-dihydro-4H-1,3-thiazin-2-yl)benzamide

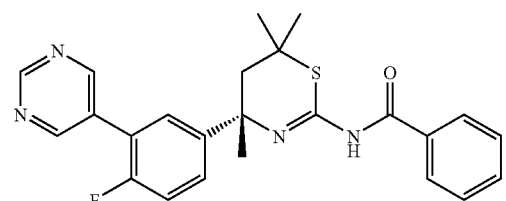

To a 97° C. solution of (S)-N-(4-(3-bromo-4-fluorophenyl)-4,6,6-trimethyl-5,6-dihydro-4H-1,3-thiazin-2-yl)benzamide (0.067 g, 0.15 mmoles, 1.0 equiv) in 1,2-dimethoxyethane (1.5 mL), ethanol (0.7 mL) and water (1.0 mL) is added pyrimidine-5-boronic acid (0.095 g, 0.77 mmoles, 5.0 equiv), cesium carbonate (0.301 g, 0.92 mmoles, 6.1 equiv) and bis(triphenylphoshine)palladium (II) chloride (0.022 g, 0.03 mmoles, 0.2 equiv). The reaction mixture is stirred at 97° C. for 20 minutes. After cooling to room temperature, the reaction mixture is poured into water and extracted with ethyl acetate. The organic phase is dried over sodium sulfate, filtered, and concentrated under reduced pressure. The solvent is removed under reduced pressure and the residue is purified by silica gel flash column chromatography eluting with a linear gradient of dichloromethane to 15% ethyl acetate: dichloromethane to give the title compound (46% yield): MS (m/z): 435 (M+1).

Preparation 27

(S)-3-(3-Bromo-phenyl)-N-methoxy-N-methyl-3-(R)-(2-methyl-propane-2-sulfinylamino)-butyramide

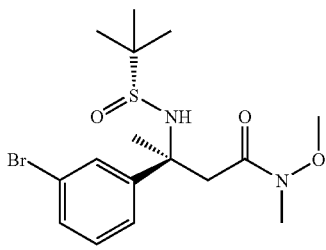

To a −78° C. solution of N,O-dimethylhydroxylamine hydrochloride (12 g, 130 mmoles, 5.0 equiv) in THF (200 mL) is added n-butyl lithium (100 mL, 250 mmoles, 10 equiv) (2.5 M in Hexanes) via cannula. The reaction is stirred for 15 minutes and a solution of (S)-3-((R)-2-methyl-propane-2-sulfinylamino)-3-phenyl-butyric acid methyl ester (9.5 g, 25 mmoles, 1.0 equiv) in THF (50 mL) is added dropwise. The reaction is warmed to −60° C., and maintained at that temperature for 1 h. The reaction is quenched with saturated aqueous ammonium chloride, diluted with water, and extracted with ethyl acetate. The organic phase is extracted with water, saturated aqueous NaCl, dried over sodium sulfate, filtered and concentrated under reduced pressure to give the title compound (60% yield): MS (m/z): 405, 407 (M+1).

The following compounds in Table 10 are prepared essentially as described in the preparation of (S)-3-(3-Bromo-phenyl)-N-methoxy-N-methyl-3-(R)-(2-methyl-propane-2-sulfinylamino)-butyramide.

TABLE 10

| Prep. No. | Chemical name | Physical data MS (m/z) |
|---|---|---|
| 27a | (S)-3-(3-bromo-4-fluorophenyl)-3-((R)-1,1-dimethylethylsulfinamido)-N-methoxy-N-methylbutanamide | 423, 425 (M + 1) |
| 27b | (S)-3-(5-bromo-2,4-difluorophenyl)-3-((R)-1,1-dimethylethylsulfinamido)-N-methoxy-N-methylbutanamide | 441, 443 (M + 1) |

Preparation 28

(R)-2-Methyl-propane-2-sulfinic acid [(S)-1-(3-bromo-phenyl)-1-methyl-3-oxo-butyl]-amide

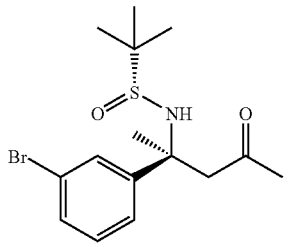

To a −78° C. solution of (S)-3-(3-bromo-phenyl)-N-methoxy-N-methyl-3-(R)-(2-methyl-propane-2-sulfinylamino)-butyramide (1.5 g, 3.7 mmoles; 1.0 equiv) in THF (53 mL) is added methylmagnesium bromide (6.2 mL, 18.5 mmoles, 5.0 equiv) and the reaction is allowed to warmed to ambient temperature. After 1 h, the reaction is cooled to −78° C. and quenched with saturated aqueous ammonium chloride. The mixture is diluted with water and extracted with ethyl acetate. The organic phase is dried over sodium sulfate, filtered, and concentrated under reduced pressure to give the title compound (>95% yield): MS (m/z) 360, 362 (M+1)

The following compounds in Table 11 are prepared essentially as described in the preparation of (R)-2-Methyl-propane-2-sulfinic acid [(S)-1-(3-bromo-phenyl)-1-methyl-3-oxo-butyl]-amide.

TABLE 11

| Prep. No. | Chemical name | Physical data MS (m/z) |
|---|---|---|
| 28a | (R)—N-((S)-2-(3-bromo-4-fluorophenyl)-4-oxopentan-2-yl)-2-methylpropane-2-sulfinamide | 378, 380 (M + 1) |
| 28b | (R)—N-((S)-2-(5-bromo-2,4-difluorophenyl)-4-oxopentan-2-yl)-2-methylpropane-2-sulfinamide | 396, 398 (M + 1) |

Preparation 29

(R)-N-((2S)-2-(3-bromophenyl)-4-hydroxypentan-2-yl)-2-methylpropane-2-sulfinamide

PG6-E01647-028

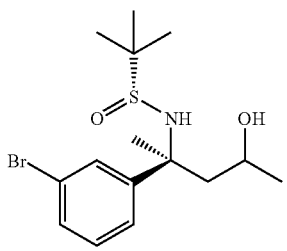

To a solution of (R)-2-methyl-propane-2-sulfinic acid [(S)-1-(3-bromo-phenyl)-1-methyl-3-oxo-butyl]-amide (1.34 g, 3.5 mmoles, 1.0 equiv) in methanol (20 mL) is added sodium tetrahydroborate (1.4 g, 35 mmoles, 10.0 equiv). The reaction is stirred at ambient temperature overnight. The reaction is carefully quenched with water and extracted ethyl acetate. The organic phase is dried over sodium sulfate and the solvent is removed under reduced pressure to give a mixture a diastereomers. The diastereomers are separated by chromatography on silica gel (120 g) eluting with a gradient of (50:50) ethyl acetate:hexane to (100:0) ethyl acetate:hexane. The second eluting isomer is isolated and the solvent removed under reduced pressure to give the title compound as a single diastereomer (45% yield): MS (m/z): 362, 364 (M+1).

The following compounds in Table 12 are prepared essentially as described in the preparation of (R)-N-((2S)-2-(3-bromophenyl)-4-hydroxypentan-2-yl)-2-methylpropane-2-sulfinamide.

TABLE 12

| Prep. No. | Chemical name | Physical data MS (m/z) |
|---|---|---|
| 29a | (R)—N-((2S)-2-(3-bromo-4-fluorophenyl)-4-hydroxypentan-2-yl)-2-methylpropane-2-sulfinamide[2] | 380, 382 (M + 1) |
| 29b | (R)—N-((2S)-2-(5-bromo-2,4-difluorophenyl)-4-hydroxypentan-2-yl)-2-methylpropane-2-sulfinamide[3] | 398, 400 (M + 1) |

[2]The title compound was isolated and used as a mixture of diastereomers.
[3]The title compound was isolated and used as a 65:35 mixture of diastereomers.

Preparation 30

(S)-4-Amino-4-(3-bromo-phenyl)-pentan-2-ol

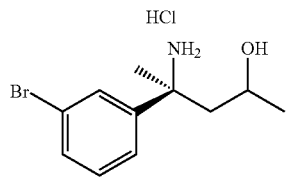

A solution of hydrogen chloride (5 mL; 13 equiv; 20 mmoles) (4 M in dioxane) and (R)-2-methyl-propane-2-sulfinic acid [(S)-1-(3-bromo-phenyl)-3-hydroxy-1-methyl-butyl]-amide (570 mg, 1.6 mmoles, 1.0 equiv) as a single diastereomer is stirred for 5 minutes. The solvent is removed under reduced pressure and the residue is made basic with saturated aqueous sodium bicarbonate. The aqueous phase is extracted with dichloromethane. The organic phase is dried over sodium sulfate, filtered, and concentrated under reduced pressure to give the title compound: MS (m/z): 358, 360 (M+1).

The following compounds in Table 13 are prepared essentially as described in the preparation of (S)-4-Amino-4-(3-bromo-phenyl)-pentan-2-ol.

TABLE 13

| Prep. No. | Chemical name | Physical data MS (m/z) |
|---|---|---|
| 30a | (4S)-4-amino-4-(5-bromo-2,4-difluorophenyl)pentan-2-ol[4] | 380, 382 (M + 1) |

[4]The title compound was isolated as a mixture of diastereomers.

Preparation 31

Tert-Butyl (4S,6R)-4-(3-bromophenyl)-4,6-dimethyl-5,6-dihydro-4H-1,3-thiazin-2-ylcarbamate

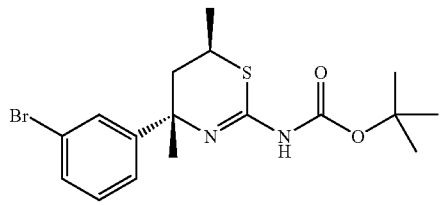

To a solution of (S)-4-amino-4-(3-bromo-phenyl)-pentan-2-ol (410 mg, 794 μmoles) as a single diastereomer in THF (10 mL) is added bis(trimethylsilyl)trifluoroacetamide (204 mg, 0.79 mmoles). After 1 h, benzoyl isothiocyanate (259 mg, 1.7 mmoles) is added dropwise. The reaction is stirred for 1 h. The reaction mixture is concentrated under reduced pressure. To the resulting residue is added 5 N hydrogen chloride (25 mL, 125 mmoles) and the reaction is heated to 100° C. After 48 h, the solvent is removed under reduced pressure and the residue is partitioned between THF (20 mL) and saturated sodium bicarbonate (10 mL). To the mixture is added di-tert-butyl dicarbonate (347 mg, 1.6 mmoles) and the reaction is stirred for 48 h. The reaction is diluted with water and extracted with dichloromethane. The organic phase is dried over sodium sulfate, filtered, and concentrated under reduced pressure. The product is purified by silica gel eluting with a linear gradient of hexane to hexane:ethyl acetate (5:2) over 20 minutes to give the title compound (52% Yield, 70% purity as determined by LCMS): MS (m/z): 399, 401 (M+1).

Preparation 32

Tert-butyl-(4S,6R)-4-(3-bromo-4-fluorophenyl)-4,6-dimethyl-5,6-dihydro-4H-1,3-thiazin-2-ylcarbamate A solution of (R)—N-((2S)-2-(3-bromo-4-fluorophenyl)-4-hydroxypentan-2-yl)-2-methylpropane-2-sulfinamide as a 1:5 mixture of diastereomers (2 g, 1.0 equiv) in dioxane (5 mL) is added dropwise to solution of 4N hydrogen chloride in dioxane (20 mL, 80 mmoles) at 0° C. The reaction is warmed to room temperature and stirred for 5 minutes. The solvent is removed under reduced pressure and the residue is made basic with saturated aqueous sodium bicarbonate. The aqueous phase is extracted with dichloromethane. The organic phase is dried over sodium sulfate, filtered, and concentrated under reduced pressure.

The resulting residue is dissolved in THF (50 mL) and cooled to 0° C. Benzoyl isothiocyanate (1.7 g, 10.5 mmoles) is added dropwise. The reaction is stirred for 1 h. The reaction mixture is concentrated under reduced pressure. The residue is dissolved in dioxane (5 mL) and transferred to a thick-walled glass reaction vessel. To the solution is added 5 N hydrogen chloride (75 mL, 375 mmoles). The reaction vessel is capped and heated to 100° C. After 24 h, the solvent is removed under reduced pressure and the residue is partitioned between THF (20 mL) and saturated aqueous sodium bicarbonate (10 mL). To the mixture is added di-tert-butyl dicarbonate (1.7 g, 7.9 mmoles) and the reaction is stirred for 2 h. The reaction mixture is diluted with water and extracted with dichloromethane. The organic phase is dried over sodium sulfate, filtered, and concentrated under reduced pressure.

The residue is purified by column chromatography using silica gel (340 g) eluting with a gradient of (0:100) Ethyl acetate:Hexane to (50:

50) Ethyl acetate:Hexane over 25 min. The second eluting diastereomer is collected and the solvent removed under reduced pressure to give 595 mg of a mixture:

Preparation 32: the title compound, tert-butyl-(4S,6R)-4-(3-bromo-4-fluorophenyl)-4,6-dimethyl-5,6-dihydro-4H-1,3-thiazin-2-ylcarbamate: MS (m/z): 417, 419 (M+1); and Preparation 32a: N-((4S,6R)-4-(3-bromo-4-fluorophenyl)-4,6-dimethyl-5,6-dihydro-4H-1,3-thiazin-2-yl)benzamide: MS (m/z) 421, 423 (M+1)

Preparation 33

(4S)-4-(5-bromo-2,4-difluorophenyl)-4,6-dimethyl-5,6-dihydro-4H-1,3-thiazin-2-amine

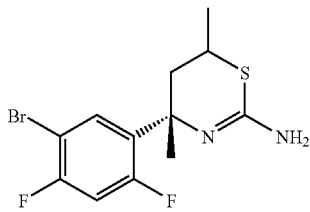

To a 0° C. solution of (4S)-4-amino-4-(5-bromo-2,4-difluorophenyl)pentan-2-ol (1.3 g, 4.4 mmoles) as a mixture of diastereomers in THF (50 mL) is added benzoyl isothiocyanate (1.4 g, 1.2 mmoles) dropwise and the reaction is stirred for 1 h. The reaction mixture is concentrated under reduced pressure. The residue is dissolved in dioxane (5 mL) and transferred to a thick-walled glass reaction vessel. To the mixture is added 5 N hydrogen chloride (75 mL, 375 mmoles) and the reaction is heated to 100° C. After 36 h, the solvent is removed under reduced pressure and the residue is dissolved in water. The water mixture is extracted with ethyl acetate. The aqueous phase is made basic with 5N NaOH and extracted with 3:1 chloroform:IPA. The chloroform: IPA phase is dried over sodium sulfate, filtered and the solvent removed under reduced pressure to give the title compound.

The ethyl acetate extract is dried over sodium sulfate, filtered and the solvent removed under reduced pressure. The resulting residue is passed through a MeOH-equilibrated SCX column, washed with methanol, followed by eluting with 2N $NH_3$ in MeOH (50 mL). The 2N $NH_3$ in MeOH wash is collected and the solvent removed under reduced pressure. The residue is combined with the title compound from the chloroform:

IPA extraction to give the title compound as a mixture of (6R and 6S) (4S)-4-(5-bromo-2,4-difluorophenyl)-4,6-dimethyl-5,6-dihydro-4H-1,3-thiazin-2-amine. (64% yield, 80% purity as determined by LCMS): MS (m/z): 335, 337 (M+1).

Preparation 34

Tert-Butyl (4S,6R)-4-(5-bromo-2,4-difluorophenyl)-4,6-dimethyl-5,6-dihydro-4H-1,3-thiazin-2-ylcarbamate

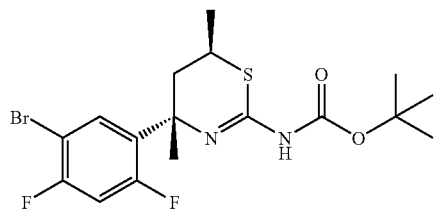

To a mixture of (6R and 6S) (4S)-4-(5-bromo-2,4-difluorophenyl)-4,6-dimethyl-5,6-dihydro-4H-1,3-thiazin-2-amine in THF (20 mL) and saturated aqueous sodium bicarbonate (10 mL) is added di-tert-butyl dicarbonate (900 mg, 4.1 mmoles). After 2 h, the reaction is diluted with water and extracted with dichloromethane. The organic phase is dried over sodium sulfate, filtered, and concentrated under reduced pressure. The product is purified by silica gel eluting with a linear gradient of hexane to hexane:ethyl acetate (4:1) over 5 minutes. The second eluting diastereomer is collected and the solvent is removed under reduced pressure to give the title: (43% yield): MS (m/z): 435, 437 (M+1).

Preparation 35

[(4S,6R)-4,6-Dimethyl-4-(3-pyrimidin-5-yl-phenyl)-5,6-dihydro-4H-[1,3]thiazin-2-yl]-carbamic Acid Tert-Butyl Ester

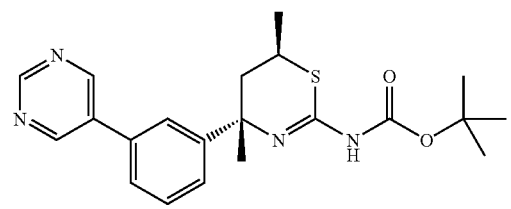

To a 100° C. solution of tert-butyl (4S,6R)-4-(3-bromophenyl)-4,6-dimethyl-5,6-dihydro-4H-1,3-thiazin-2-ylcarbamate in 1,2-dimethoxyethane: water: ethanol [(3:1.5:1), 12 mL] is added, in a single portion, pyrimidine-5-boronic acid (128 mg, 5.9 mmoles, 2.5 equiv), bis(triphenylphosphine)palladium(II) chloride (29 mg, 41 μmoles, 0.1 equiv) and cesium carbonate (1.24 g, 1.24 mmoles, 3 equiv). After 20 minutes, the reaction is cooled to ambient temperature, diluted with water, and extracted with dichloromethane. The organic phase is dried over sodium sulfate, filtered, and concentrated under reduced pressure. The residue is purified by silica gel flash column chromatography eluting with a linear gradient of hexane to hexane:ethyl acetate (5:2) over 20 minutes to give the title compound (39% yield): MS (m/z): 399 (M+1).

The following compounds in Table 14 are prepared essentially as described in the preparation of [(4S,6R)-4,6-dimethyl-4-(3-pyrimidin-5-yl-phenyl)-5,6-dihydro-4H-[1,3]thiazin-2-yl]-carbamic acid tert-butyl ester.

TABLE 14

| Prep. No. | Chemical name | Physical data MS (m/z) |
|---|---|---|
| 35a | tert-butyl (4S,6R)-4-(4-fluoro-3-(pyrimidin-5-yl)phenyl)-4,6-dimethyl-5,6-dihydro-4H-1,3-thiazin-2-ylcarbamate[5] | 417 (M + 1) |
| 35b | tert-butyl (4S,6R)-4-(2,4-difluoro-5-(pyrimidin-5-yl)phenyl)-4,6-dimethyl-5,6-dihydro-4H-1,3-thiazin-2-ylcarbamate | 435 (M + 1) |

[5]Isolated as a mixture of title compound and N-((4S,6R)-4-(3-bromo-4-fluorophenyl)-4,6-dimethyl-5,6-dihydro-4H-1,3-thiazin-2-yl)benzamide. MS (m/z): 421 (M + 1).

Preparation 36

1-bromo-3-(prop-1-en-2-yl)benzene

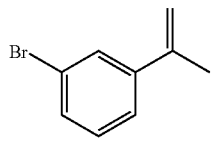

Methyltriphenylphosphonium bromide (35.7 g, 97.9 mmoles, 1.3 equiv) is suspended in tetrahydrofuran (100 mL) and cooled to 0° C. N-Butyllithium (2.5M in hexanes, 27.0 g, 97.7 mmoles, 39.2 mL, 1.3 equiv) is added slowly to the mixture via an addition funnel. The resulting solution is stirred for 1 h at 0° C. A solution of 3-bromoacetophenone (15.0 g, 75.3 mmoles, 10.0 mL, 1.0 equiv) in tetrahydrofuran (50 mL) is added slowly via an addition funnel. The resulting mixture is warmed to room temperature and stirred for 3 h. The reaction is cooled to 0° C. and quenched with saturated aqueous ammonium chloride solution. The layers are partitioned in a separatory funnel and the aqueous phase is extracted with hexanes. The combined organic phase is dried over anhydrous sodium sulfate, filtered, and allowed to stand overnight at room temperature. The organic phase is decanted from a precipitate and concentrated under reduced pressure. The resulting solid is diluted with hexanes and filtered. The precipitate is washed with hexanes. The filtrate is concentrated and the resulting mixture is purified by silica gel flash column chromatography (hexanes) to give the title compound (83% yield): $^1$H NMR (CDCl$_3$, 400 MHz) δ 7.59 (t, 1H, J=1.72 Hz), 7.40-7.36 (m, 2H), 7.18 (t, 1H, J=8 Hz), 5.36 (s, 1H), 5.12-5.10 (m, 1H), 2.13-3.11 (m, 3H).

The following compound in Table 15 is prepared essentially according to the preparation of 1-bromo-3-(prop-1-en-2-yl)benzene.

TABLE 15

| Prep. No. | Chemical name | Physical data |
|---|---|---|
| 36a | 2-bromo-1-fluoro-4-(prop-1-en-2-yl)benzene | See below[6] |

[6]$^1$H NMR(CDCl$_3$, 400 MHz): δ 7.61 (dd, 1H, J = 6.8, 2.2 Hz), 7.36-7.32 (m, 1H), 7.05 (t, 1H, J = 8.4 Hz), 5.29 (s, 1H), 5.09-5.07 (m, 1H), 2.10-2.09 (m, 3H)

Preparation 37

Ethyl 4-(3-bromophenyl)-2-hydroxypent-4-enoate

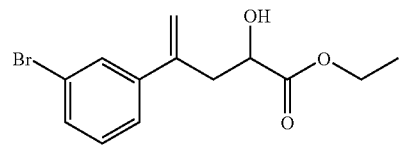

To a solution of 2-bromo-1-fluoro-4-(prop-1-en-2-yl)benzene (12.3 g, 62.2 mmol, 1.0 equiv) in acetonitrile (124 mL, 0.5 M) are added ethyl glyoxalate (38.1 g, 37 mL, 187 mmoles, 3 equiv) and ytterbium trifluoromethanesulfonate, hydrate (7.72 g, 12.4 mmoles, 0.2 equiv). The mixture is stirred overnight at room temperature. The mixture is concentrated under reduced pressure and diluted with diethyl ether. The resulting solution is washed twice with water. The organic layer is dried over anhydrous sodium sulfate, filtered, and concentrated under reduced pressure. The residue is purified via flash column chromatography on silica gel (330 g) in two batches using a gradient of 0-100% ethyl acetate/hexanes to yield the title compound (87% yield): $^1$H NMR (CDCl$_3$, 400 MHz): δ 7.53 (t, 1H, J=1.9 Hz), 7.41-7.37 (dt, 1H), 7.33-7.30 (dt, 1H), 7.18 (t, 1H, J=7.6 Hz), 5.37 (s, 1H), 5.22 (s, 1H), 4.26-4.21 (m, 1H), 4.17-3.99 (m, 2H), 2.99 (dd, J=14.8, 4.8 Hz), 2.83-2.72 (m, 2H), 1.23 (t, 3H, J=7.6 Hz).

The following compound in Table 16 is prepared essentially according to the preparation of ethyl 4-(3-bromophenyl)-2-hydroxypent-4-enoate.

TABLE 16

| Prep. No. | Chemical name | Physical data |
|---|---|---|
| 37a | ethyl 4-(3-bromo-4-fluorophenyl)-2-hydroxypent-4-enoate | See below[7] |

[7]$^1$H NMR(CDCl$_3$, 400 MHz): δ 7.59-7.55 (m, 1H), 7.32-7.27 (m, 1H), 7.08-7.03 (m, 1H), 5.33 (s, 1H), 5.20 (s, 1H), 4.26-4.20 (m, 1H), 4.19-4.02 (m, 2H), 2.96 (dd, J = 14.8, 4.8 Hz), 2.80-2.73 (m, 2H), 1.24 (t, 3H, J = 7.6 Hz)

Preparation 38

Ethyl 2-amino-4-(3-bromophenyl)-4-methyl-5,6-dihydro-4H-1,3-thiazine-6-carboxylate

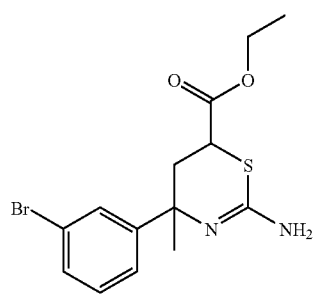

To a solution of ethyl 4-(3-bromophenyl)-2-hydroxypent-4-enoate (5.1 g, 17 mmoles) in acetonitrile (68 mL) is added 2,6-lutidine (2.19 g, 20.4 mmol, 1.2 equiv). The reaction is cooled to 0° C. and trifluoromethanesulfonic anhydride (3.30 mL, 19.6 mmol, 1.15 equiv) is added dropwise over approximately 5 minutes. The mixture is stirred at 0° C. for 20 minutes. Thiourea (2.59 g, 34.0 mmol, 2 equiv) is added and the reaction is warmed to room temperature. After 45 minutes, the mixture is concentrated under reduced pressure. The resulting viscous orange oil is then added via large pipette to stirring sulfuric acid (17.8 M, 8 mL) at room temperature. After 20 minutes, the mixture is added dropwise to a vigorously stirring, 0° C. solution of $K_2CO_3$ (ca. 50 g) in 50 mL $H_2O$). Additional water is added to enable stirring upon solid formation during the quench. The tan/orange solid is collected by filtration. The solid is allowed to dry on the filter paper by a stream of air for 1 h to give the title compound as a mixture of diastereomers which is used without further purification: MS (m/z): 357, 359 (M+1).

The following compound in Table 17 is prepared essentially as described in the preparation of ethyl 2-amino-4-(3-bromophenyl)-4-methyl-5,6-dihydro-4H-1,3-thiazine-6-carboxylate.

TABLE 17

| Prep. No. | Chemical name | Physical data MS (m/z) |
|---|---|---|
| 38a | ethyl 2-amino-4-(3-bromo-4-fluorophenyl)-4-methyl-5,6-dihydro-4H-1,3-thiazine-6-carboxylate[8] | 375, 377 (M + 1) |

[8]Racemic diastereomers

Preparation 39

Ethyl 4-(3-bromophenyl)-2-(tert-butoxycarbonylamino)-4-methyl-5,6-dihydro-4H-1,3-thiazine-6-carboxylate

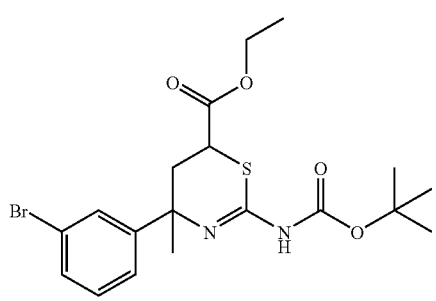

To a suspension of ethyl 2-amino-4-(3-bromophenyl)-4-methyl-5,6-dihydro-4H-1,3-thiazine-6-carboxylate (6.1 g, 17 mmol) in 1,4-dioxane (35 mL), water (18 mL), and saturated aqueous sodium bicarbonate (18 mL) is added di-t-butyldicarbonate (7.42 g, 34.0 mmol, 2 equiv). The mixture is stirred for ca. 60 h. The reaction is diluted with water and extracted three times with $CH_2Cl_2$. The organic layer is dried over $Na_2SO_4$, filtered, and concentrated under reduced pressure to give a brown oil. The oil is purified by flash column chromatography on silica gel (150 g) eluting with a gradient of 0 to 100% ethyl acetate/hexane to give the title compound as a mixture of diastereomers (64% yield): MS (m/z): 457, 459 (M+1)

The following compound in Table 18 is prepared essentially according to the preparation of ethyl 4-(3-bromophenyl)-2-(tert-butoxycarbonylamino)-4-methyl-5,6-dihydro-4H-1,3-thiazine-6-carboxylate.

TABLE 18

| Prep. No. | Chemical name | Physical data MS (m/z) |
|---|---|---|
| 39a | ethyl 4-(3-bromo-4-fluorophenyl)-2-(tert-butoxycarbonylamino)-4-methyl-5,6-dihydro-4H-1,3-thiazine-6-carboxylate[9] | 475, 477 (M + 1) |

[9]Racemic diastereomers

Preparation 40

(4S,6S)-Ethyl 4-(3-bromophenyl)-2-(tert-butoxycarbonylamino)-4-methyl-5,6-dihydro-4H-1,3-thiazine-6-carboxylate

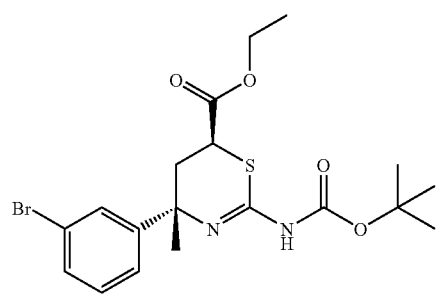

Ethyl 4-(3-bromophenyl)-2-(tert-butoxycarbonylamino)-4-methyl-5,6-dihydro-4H-1,3-thiazine-6-carboxylate (3.5 g, 7.7 mmol) is purified by chiral HPLC in two stages: (Column: Chiralcel OJ 8×32 cm; Eluent: 1:3 (3A alcohol: heptane); Flow: 400 mL/min at UV 240 nm), providing cut 1 containing peaks 1 and 2 of 3; then peaks 1 and 2 are further purified by additional chiral chromatography (Column: Chiralcel OD 8×32 cm; Eluent 1:9 (isopropyl alcohol: heptane); Flow: 400 mL/min at UV 240 nm). Isolation of the second eluting isomer provides the title compound after concentration of the fractions under reduced pressure (14% yield).

Preparation 41

(+/−) Tert-Butyl (4S,6S)-4-(3-bromophenyl)-6-(hydroxymethyl)-4-methyl-5,6-dihydro-4H-1,3-thiazin-2-ylcarbamate

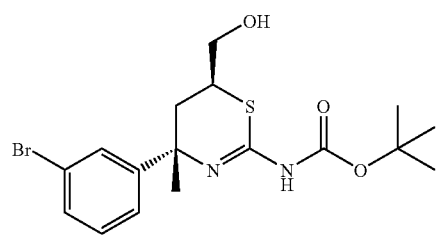

To a 0° C. solution of ethyl 4-(3-bromophenyl)-2-(tert-butoxycarbonylamino)-4-methyl-5,6-dihydro-4H-1,3-thiazine-6-carboxylate (2.0 g, 4.4 mmol) in tetrahydrofuran (87 mL) and ethanol (25 mL) is added lithium borohydride (289 mg, 13.1 mmol, 3 equiv). The reaction is warmed to room temperature and stirred for 4 h. The reaction mixture is quenched with saturated $NH_4Cl$. The layers are separated and the aqueous layer is extracted with ethyl acetate. The combined organic layers are washed with saturated aqueous NaCl and dried over $Na_2SO_4$. The mixture is filtered and concentrated to give a light yellow oil. The oil is purified by column chromatography on silica gel (120 g) using a gradient of 0 to 100% ethyl acetate/hexane to give the title compound (29% yield): MS (m/z): 415, 417 (M+1).

Preparation 42

Tert-Butyl (4S,6S)-4-(3-bromophenyl)-6-(hydroxymethyl)-4-methyl-5,6-dihydro-4H-1,3-thiazin-2-ylcarbamate (+/−) Tert-butyl (4S,6S)-4-(3-bromophenyl)-6-(hydroxymethyl)-4-methyl-5,6-dihydro-4H-1,3-thiazin-2-ylcarbamate (870 mg, 2.1 mmol) is purified by HPLC chiral separation: (Column: Chiralpak AD 8×36 cm×20 μm; Eluent: 100% 3A ethyl alcohol; Flow: 400 mL/min at UV 250 nm). The second eluting isomer is isolated to provide the enantiomerically enriched title compound (38.5% yield): MS (m/z): 415, 417 (M+1).

Preparation 43

(+/−) Tert-Butyl (4S,6S)-6-(hydroxymethyl)-4-methyl-4-(3-(pyrimidin-5-yl)phenyl)-5,6-dihydro-4H-1,3-thiazin-2-ylcarbamate

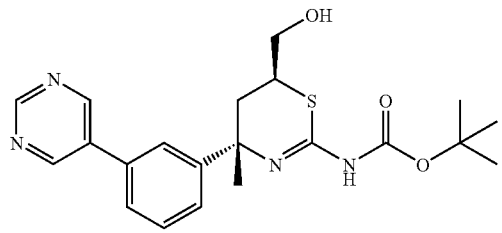

To a 110° C. solution of (+/−) tert-butyl (4S,6S)-4-(3-bromophenyl)-6-(hydroxymethyl)-4-methyl-5,6-dihydro-4H-1,3-thiazin-2-ylcarbamate (150 mg, 0.36 mmol) in 1,2-dimethoxyethane (4.5 mL), ethanol (1.5 mL), and water (2.3 mL) is added pyrimidine-5-boronic acid (112 mg, 0.90 mmoles, 2.5 equiv), cesium carbonate (353 mg, 1.08 mmol, 3 equiv), and bis(triphenylphosphine)palladium(II) chloride (25 mg, 0.036 mmol, 0.1 equiv). The reaction is stirred at 110° C. After 20 minutes, the reaction mixture is diluted with EtOAc and $H_2O$. The layers are separated and the aqueous phase is extracted with EtOAc. The combined organic layers are dried over sodium sulfate, filtered, and concentrated under reduced pressure. The crude residue is purified by column chromatography on silica gel (5% MeOH/DCM) to give the title compound (29% yield): MS (m/z): 415 (M+1)

The following compound in Table 19 is prepared essentially according to the preparation of (+/−) tert-butyl (4S,6S)-6-(hydroxymethyl)-4-methyl-4-(3-(pyrimidin-5-yl)phenyl)-5,6-dihydro-4H-1,3-thiazin-2-ylcarbamate.

TABLE 19

| Prep. No. | Chemical name | Physical data MS (m/z) |
|---|---|---|
| 43a | tert-butyl (4S,6S)-4-(3-bromophenyl)-6-(hydroxymethyl)-4-methyl-5,6-dihydro-4H-1,3-thiazin-2-ylcarbamate | 415 (M + 1) |

Preparation 44

(+/−) Tert-Butyl (4S,6S)-4-(3-bromophenyl)-6-(2-hydroxypropan-2-yl)-4-methyl-5,6-dihydro-4H-1,3-thiazin-2-ylcarbamate

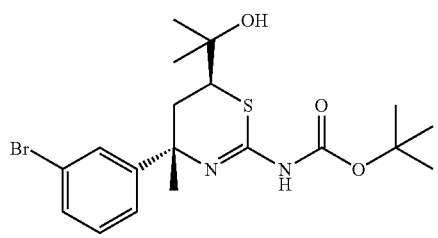

To a 0° C. solution of ethyl 2-amino-4-(3-bromophenyl)-4-methyl-5,6-dihydro-4H-1,3-thiazine-6-carboxylate (250 mg, 0.55 mmol) in tetrahydrofuran (5.5 mL) is added methylmagnesium chloride (0.58 mL, 1.75 mmol, 3.2 equiv). After 15 minutes, additional methylmagnesium chloride (0.38 mL, 1.2 mmol, 2 equiv) is added. After 30 minutes, the reaction mixture is quenched with saturated aqueous $NH_4Cl$ and diluted with ethyl acetate. The layers are separated and the aqueous layer is extracted with ethyl acetate. The combined organic layers are washed with saturated aqueous NaCl, dried over $Na_2SO_4$, filtered, and concentrated under reduced pressure. The crude residue is purified by column chromatography on silica gel (80 g) eluting with a gradient of 0 to 100% ethyl acetate/hexanes to give the title compound (26% yield): MS (m/z): 443, 445 (M+1).

The following compounds in Table 20 are prepared essentially according to the preparation of (+/−) tert-butyl (4S,6S)-4-(3-bromophenyl)-6-(2-hydroxypropan-2-yl)-4-methyl-5,6-dihydro-4H-1,3-thiazin-2-ylcarbamate.

TABLE 20

| Prep. No. | Chemical name | Physical data MS (m/z) |
|---|---|---|
| 44a | (+/−) tert-butyl (4S,6S)-4-(3-bromo-4-fluorophenyl)-6-(2-hydroxypropan-2-yl)-4-methyl-5,6-dihydro-4H-1,3-thiazin-2-ylcarbamate | 461, 463 (M + 1) |
| 44b | tert-butyl (4S,6S)-4-(3-bromophenyl)-6-(2-hydroxypropan-2-yl)-4-methyl-5,6-dihydro-4H-1,3-thiazin-2-ylcarbamate | 443, 445 (M + 1) |

Preparation 45

(+/−) Tert-Butyl (4S,6S)-4-(4-fluoro-3-(pyrimidin-5-yl)phenyl)-6-(2-hydroxypropan-2-yl)-4-methyl-5,6-dihydro-4H-1,3-thiazin-2-ylcarbamate

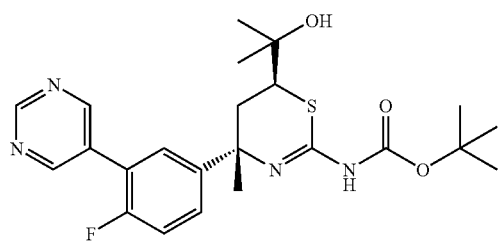

To a 100° C. solution of tert-butyl (4S,6S)-4-(3-bromo-4-fluorophenyl)-6-(2-hydroxypropan-2-yl)-4-methyl-5,6-dihydro-4H-1,3-thiazin-2-ylcarbamate (1.11 g, 2.41 mmoles, 1.0 equiv) in 1,2-dimethoxyethane (22 mL) and water (7 mL) are added pyrimidine-5-boronic acid (1.2 g, 9.6 mmol, 4 equiv), bis(triphenylphosphine)palladium(II) chloride (508 mg, 0.723 mmol, 0.3 equiv), and cesium carbonate (2.36 g, 7.2 mmol, 3 equiv). After 25 min, the mixture is cooled to room temperature. The reaction mixture is diluted with EtOAc and partitioned between EtOAc and water. The aqueous phase is extracted 3 times with EtOAc. The combined organic phase is dried over sodium sulfate, filtered, and concentrated under reduced pressure to yield the crude product. The crude residue is purified by column chromatography on silica gel (80 g) eluting with EtOAc to yield:

Preparation 45: the title compound, (460 mg, 41% yield): MS (m/z): 461 (M+1); and Preparation 45a: (+/−) 2-((4S,6S)-2-amino-4-(4-fluoro-3-(pyrimidin-5-yl)phenyl)-4-methyl-5,6-dihydro-4H-1,3-thiazin-6-yl)propan-2-ol, (145 mg): MS (m/z): 361 (M+1).

The following compounds in Table 21 are prepared essentially according to the preparation of (+/−) tert-butyl (4S,6S)-4-(4-fluoro-3-(pyrimidin-5-yl)phenyl)-6-(2-hydroxypropan-2-yl)-4-methyl-5,6-dihydro-4H-1,3-thiazin-2-ylcarbamate.

TABLE 21

| Prep. No. | Chemical name | Physical data MS (m/z) |
|---|---|---|
| 45b | (+/−) tert-butyl (4S,6S)-6-(2-hydroxypropan-2-yl)-4-methyl-4-(3-(pyrimidin-5-yl)phenyl)-5,6-dihydro-4H-1,3-thiazin-2-ylcarbamate[10] | 443 (M + 1) |
| 45c | tert-butyl (4S,6S)-6-(2-hydroxypropan-2-yl)-4-methyl-4-(3-(pyrimidin-5-yl)phenyl)-5,6-dihydro-4H-1,3-thiazin-2-ylcarbamate | 443 (M + 1) |

[10]Racemic compound prepared and purified via chiral chromatography conditions described below in Preparation 45.

Preparation 46

Tert-Butyl (4S,6S)-4-(4-fluoro-3-(pyrimidin-5-yl)phenyl)-6-(2-hydroxypropan-2-yl)-4-methyl-5,6-dihydro-4H-1,3-thiazin-2-ylcarbamate

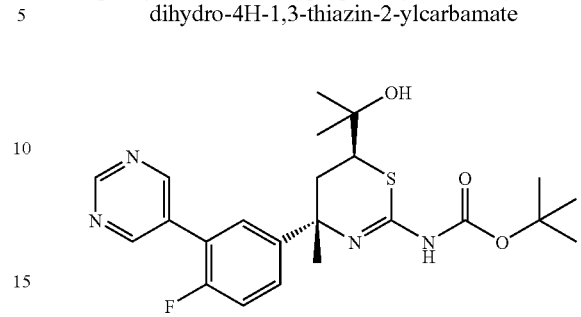

(+/−) Tert-butyl (4S,6S)-4-(4-fluoro-3-(pyrimidin-5-yl)phenyl)-6-(2-hydroxypropan-2-yl)-4-methyl-5,6-dihydro-4H-1,3-thiazin-2-ylcarbamate (455 mg, 0.99 mmol) is purified by HPLC chiral separation (Column: Chiralpak AD-H 2.1×25 cm×5 μm; Eluent: 20% EtOH/CO$_2$; Flow: 70 mL/min at UV 225 nm). The second eluting isomer is isolated to provide the enantiomerically enriched title compound (29%): MS (m/z): 461 (M+1).

EXAMPLES

Example 1

(S)-4-(3-(2-fluoropyridin-3-yl)phenyl)-4-methyl-5,6-dihydro-4H-1,3-thiazin-2-amine Dihydrochloride Salt

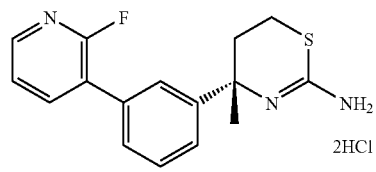

To a solution of (S)-4-(3-(2-fluoropyridin-3-yl)phenyl)-4-methyl-5,6-dihydro-4H-1,3-thiazin-2-amine (160 mg, 0.531 mmoles) in THF (4 mL) is added a saturated solution of HCl in dioxane (2 mL) at 0° C. The reaction mixture is allowed to stir at room temperature for 4 h. The solvent is removed under reduced pressure. The resulting solid is washed repeatedly with anhydrous ether and dried under reduced pressure to give title compound (87% yield): MS (m/z): 302 (M+1).

Example 2

(S)-4-[3-(5-Chloro-2-fluoro-pyridin-3-yl)-phenyl]-4-methyl-5,6-dihydro-4H-[1,3]thiazin-2-ylamine Dihydrochloride

2785443, PG6-E01268-074

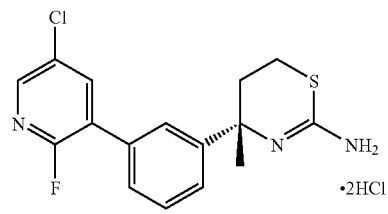

A solution of (S)-N-{4-[3-(5-Chloro-2-fluoro-pyridin-3-yl)-phenyl]-4-methyl-5,6-dihydro-4H-[1,3]thiazin-2-yl}-acetamide (430 mg, 1.1 mmoles) in trifluoroacetic acid (50 mL) and methanol (50 mL) is stirred for 8 h at 60° C. The solvent is removed under reduced pressure. The residue is dissolved in water and neutralized with saturated bicarbonate and extracted with ethyl acetate. The organic phase is dried over sodium sulfate, filtered, and concentrated under reduced pressure to give a residue. The residue is purified by silica gel flash column chromatography eluting with ethyl acetate. The resulting amine is dissolved in dichloromethane and HCl gas is bubbled through the solution for 30 seconds. The solvent is removed under reduced pressure to give the title compound (52%): MS (m/z): 336 (M+1).

The following compounds in Table 22 are prepared essentially as described in the preparation of (S)-4-[3-(5-chloro-2-fluoro-pyridin-3-yl)-phenyl]-4-methyl-5,6-dihydro-4H-[1,3]thiazin-2-ylamine dihydrochloride.

TABLE 22

| Ex. No. | Chemical name | Physical data MS (m/z) |
|---|---|---|
| 3 | (S)-4-(4-fluoro-3-(3-fluoropyrazin-2-yl)phenyl)-4-methyl-5,6-dihydro-4H-1,3-thiazin-2-amine hydrochloride[11] | 321 (M + 1) |
| 4 | (S)-4-(2,4-difluoro-5-(3-fluoropyrazin-2-yl)phenyl)-4-methyl-5,6-dihydro-4H-1,3-thiazin-2-amine hydrochloride[11] | 339 (M + 1) |

[11]Purified by reverse phase preparative HPLC: method A

Example 5

(S)-4-(2,4-Difluoro-5-pyrimidin-5-yl-phenyl)-4-methyl-5,6-dihydro-4H-[1,3]thiazin-2-ylamine

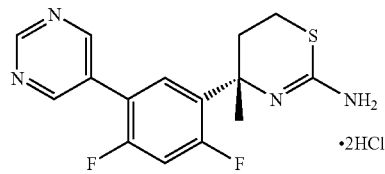

Into a solution of (S)-[4-(2,4-difluoro-5-pyrimidin-5-yl-phenyl)-4-methyl-5,6-dihydro-4H-[1,3]thiazin-2-yl]-carbamic acid tert-butyl ester (263 mg, 625 μmoles) in dichloromethane (15 mL) at ambient temperature is bubbled HCl gas for 1 minute. The reaction is sealed with a septum and stirred 18 h. The solvent is removed under reduced pressure to give the title compound (>95% Yield): MS (m/z): 321 (M+1).

The following compounds in Table 23 are prepared essentially according to the preparation of (S)-4-(2,4-difluoro-5-pyrimidin-5-yl-phenyl)-4-methyl-5,6-dihydro-4H-[1,3]thiazin-2-ylamine.

TABLE 23

| Ex. No. | Chemical name | Physical data MS (m/z) |
|---|---|---|
| 6 | (S)-4-(4-Fluoro-3-pyrimidin-5-yl-phenyl)-4-methyl-5,6-dihydro-4H-[1,3]thiazin-2-ylamine dihydrochloride | 303 (M + 1) |
| 7 | (S)-4-(2-Fluoro-5-pyrimidin-5-yl-phenyl)-4-methyl-5,6-dihydro-4H-[1,3]thiazin-2-ylamine dihydrochloride | 303 (M + 1) |
| 8 | (S)-4-[4-Fluoro-3-(2-fluoro-pyridin-3-yl)-phenyl]-4-methyl-5,6-dihydro-4H-[1,3]thiazin-2-ylamine hydrochloride[12] | 320 (M + 1) |
| 9 | (S)-4-(2,4-difluoro-5-(2-fluoropyridin-3-yl)phenyl)-4-methyl-5,6-dihydro-4H-1,3-thiazin-2-amine hydrochloride[13] | 338 (M + 1) |
| 10 | (S)-4-(2-chloro-5-(5-chloro-2-fluoropyridin-3-yl)phenyl)-4-methyl-5,6-dihydro-4H-1,3-thiazin-2-amine hydrochloride[14] | 370, 372 (M + 1) |
| 11 | (S)-4-(2,4-difluoro-5-(5-fluoropyridin-3-yl)phenyl)-4-methyl-5,6-dihydro-4H-1,3-thiazin-2-amine dihydrochloride | 338 (M + 1) |
| 12 | (S)-4-(4-fluoro-3-(pyrazin-2-yl)phenyl)-4-methyl-5,6-dihydro-4H-1,3-thiazin-2-amine dihydrochloride[13] | 303 (M + 1) |
| 13 | (+/−) ((4S,6S)-2-amino-4-methyl-4-(3-(pyrimidin-5-yl)phenyl)-5,6-dihydro-4H-1,3-thiazin-6-yl)methanol | 315 (M + 1) |
| 14 | ((4S,6S)-2-amino-4-methyl-4-(3-(pyrimidin-5-yl)phenyl)-5,6-dihydro-4H-1,3-thiazin-6-yl)methanol | 315 (M + 1) |
| 15 | (4S,6R)-4,6-dimethyl-4-(3-(pyrimidin-5-yl)phenyl)-5,6-dihydro-4H-1,3-thiazin-2-amine dihydrochloride[13] | 299 (M + 1) |
| 16 | (4S,6R)-4-(2,4-difluoro-5-(pyrimidin-5-yl)phenyl)-4,6-dimethyl-5,6-dihydro-4H-1,3-thiazin-2-amine dihydrochloride[13] | 335 (M + 1) |
| 17 | (+/−) 2-((4S,6S)-2-amino-4-(4-fluoro-3-(pyrimidin-5-yl)phenyl)-4-methyl-5,6-dihydro-4H-1,3-thiazin-6-yl)propan-2-ol | 361 (M + 1) |

[12]Purified by crystallization from acetonitrile
[13]Purified by reverse phase preparative HPLC, method A
[14]1M HCl in ether used instead of HCl (g)

Example 18

(S)-4-Methyl-4-(3-pyrimidin-5-yl-phenyl)-5,6-dihydro-4H-[1,3]thiazin-2-ylamine Dihydrochloride A solution of (S)-N-[4-Methyl-4-(3-pyrimidin-5-yl-phenyl)-5,6-dihydro-4H-[1,3]thiazin-2-yl]-acetamide (2.7 g, 8.3 mmoles, 1.0 equiv) is stirred in 5N hydrogen chloride (50 mL, 250 mmoles, 30 equiv) at 100° C. for 2 h. The reaction is cooled and the volatiles are removed under reduced pressure. The resulting residue is dissolved in water and extracted with ethyl acetate. The aqueous phase is neutralized with saturated aqueous sodium bicarbonate and extracted ethyl acetate. The organic phase is dried over sodium sulfate, filtered, and concentrated under reduced pressure to give a residue. The residue is filtered through a silica gel plug and washed with ethyl acetate. The silica gel plug is further washed with ethyl acetate containing ethyl acetate and 10% isopropyl amine. The 10% isopropyl amine in ethyl acetate wash is collected and the solvent removed under reduced pressure. The resulting free amine is dissolved in a solution of 100 mL of water containing 14 mL of 1 N HCl. The resulting solution is freeze dried to give the title compound (81% yield): MS (m/z): 285 (M+1).

The following compounds in Table 24 are prepared essentially as described in the preparation of (S)-4-methyl-4-(3-pyrimidin-5-yl-phenyl)-5,6-dihydro-4H-[1,3]thiazin-2-ylamine dihydrochloride.

TABLE 24

| Ex. No. | Chemical name | Physical data MS (m/z) |
|---|---|---|
| 19 | (S)-4-[3-(5-Methoxy-pyridin-3-yl)-phenyl]-4-methyl-5,6-dihydro-4H-[1,3]thiazin-2-ylamine dihydrochloride[15] | 314 (M + 1) |
| 20 | 4-[3-(5-Methoxy-pyridin-3-yl)-phenyl]-4-methyl-5,6-dihydro-4H-[1,3]thiazin-2-ylamine dihydrogen chloride | 314 (M + 1) |
| 21 | (S)-4-(4-fluoro-3-(pyrimidin-5-yl)phenyl)-4,6,6-trimethyl-5,6-dihydro-4H-1,3-thiazin-2-amine[16] | 331 (M + 1) |

[15]Purified by crystallization of the crude HCl salt from 2-5% methanol in acetonitrile.
[16]Purified by HPLC, method A

Example 22

(4S,6R)-4-(4-fluoro-3-(pyrimidin-5-yl)phenyl)-4,6-dimethyl-5,6-dihydro-4H-1,3-thiazin-2-amine Dihydrochloride Into a 1:1 mixture of tert-butyl (4S,6R)-4-(4-fluoro-3-(pyrimidin-5-yl)phenyl)-4,6-dimethyl-5,6-dihydro-4H-1,3-thiazin-2-ylcarbamate and N-((4S,6R)-4-(3-bromo-4-fluorophenyl)-4,6-dimethyl-5,6-dihydro-4H-1,3-thiazin-2-yl)benzamide (360 mg) in dichloromethane (10 mL) at ambient temperature is bubbled HCl gas for 1 minute. The reaction is sealed with a septum and stirred 18 h. The solvent is removed under reduced pressure. The resulting residue is dissolved in water and extracted with ethyl acetate. The organic phase is dried over sodium sulfate, filtered, and concentrated under reduced pressure to give N-((4S,6R)-4-(3-bromo-4-fluorophenyl)-4,6-dimethyl-5,6-dihydro-4H-1,3-thiazin-2-yl)benzamide as a residue. To the resulting residue is added 5 N HCl (5 mL) and the reaction is heated to 100° C. for 2 h. The solvent is removed under reduced pressure to give crude title compound.

The aqueous phase from the initial ethyl acetate wash is neutralized with saturated sodium bicarbonate and extracted with (3:1) CHCl$_3$:isopropyl alcohol. The organic phase is dried over sodium sulfate, filtered, and concentrated under reduced pressure. This material is combined with the crude product and is purified by preparative HPLC: Xterra® RP18 (30×300 mm) column at ambient temperature and a flow of 40 mL/min. The elution system consists of an isocratic gradient of 0:100 (acetonitrile: (0.1% HCl in H$_2$O)) for 1-5 min followed by a linear gradient from 10:90 (acetonitrile: (0.1% HCl in H$_2$O)) to 30:70 (acetonitrile: (0.1% HCl in H$_2$O)) over 20 min. The fractions are combined and concentrated under reduced pressure to give the title compound (50% yield): MS (m/z): 317 (M+1).

Example 23

(+/−) 2-((4S,6S)-2-amino-4-(4-fluoro-3-(pyrimidin-5-yl)phenyl)-4-methyl-5,6-dihydro-4H-1,3-thiazin-6-yl)propan-2-ol Hydrogen chloride gas is bubbled through a solution of (+/−) tert-butyl (4S,6S)-6-(2-hydroxypropan-2-yl)-4-methyl-4-(3-(pyrimidin-5-yl)phenyl)-5,6-dihydro-4H-1,3-thiazin-2-ylcarbamate (33 mg, 0.075 mmol) in dichloromethane (5 mL) and the resulting mixture is sealed and stirred for 16 h at room temperature. The reaction mixture is concentrated under reduced pressure and purified by passage through a MeOH-equilibrated SCX column, eluting with 7N NH$_3$ in MeOH. The resulting free base is dissolved in MeOH and 1N HCl in Et$_2$O (approx. 5 equiv) is added. The mixture is concentrated and co-evaporated with Et$_2$O twice to yield the title compound (87% yield): MS (m/z): 343 (M+1).

Example 24

2-((4S,6S)-2-amino-4-(4-fluoro-3-(pyrimidin-5-yl)phenyl)-4-methyl-5,6-dihydro-4H-1,3-thiazin-6-yl)propan-2-ol

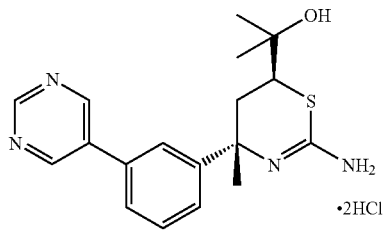

A solution of tert-butyl (4S,6S)-6-(2-hydroxypropan-2-yl)-4-methyl-4-(3-(pyrimidin-5-yl)phenyl)-5,6-dihydro-4H-1,3-thiazin-2-ylcarbamate (221 mg, 0.50 mmol) in trifluoroacetic acid (2 mL) is stirred at room temperature for 80 min. The mixture is added directly to a MeOH-equilibrated SCX column. The column is washed with MeOH (100 mL) and the product is eluted with 7N NH$_3$ in MeOH (100 mL). The solution is concentrated under reduced pressure. The residue is diluted with CH$_2$Cl$_2$ and HCl (g) is bubbled through for 5 min. The reaction mixture is concentrated to give the title compound (67.5% yield): MS (m/z): 343 (M+1).

The following compound in Table 25 is prepared essentially as described in the preparation of 2-((4S,6S)-2-amino-4-(4-fluoro-3-(pyrimidin-5-yl)phenyl)-4-methyl-5,6-dihydro-4H-1,3-thiazin-6-yl)propan-2-ol.

TABLE 25

| Ex. No. | Chemical name | Physical data MS (m/z) |
|---|---|---|
| 25 | 2-((4S,6S)-2-amino-4-(4-fluoro-3-(pyrimidin-5-yl)phenyl)-4-methyl-5,6-dihydro-4H-1,3-thiazin-6-yl)propan-2-ol | 362 (M + 1) |

In Vitro Assay Procedures:

For in vitro enzymatic and cellular assays, test compounds are prepared in DMSO to make up a 10 mM stock solution. The stock solution is serially diluted in DMSO to obtain a ten-point dilution curve with final compound concentrations ranging from 10 mM to 1 pM in a 96-well round-bottom plate before conducting the in vitro enzymatic and whole cell assays.

In Vitro Protease Inhibition Assays:

Bace FRET Assay

Serial dilutions of test compounds are prepared as described above. Compounds are further diluted 20× in $KH_2PO_4$ buffer. Ten µL of each dilution is added to each well on row A to H of a corresponding low protein binding black plate containing the reaction mixture (25 µL of 50 mM $KH_2PO_4$, pH 4.6, 1 mM TRITON® X-100, 1 mg/mL Bovine Serum Albumin, and 15 µM of FRET substrate) (See Yang, et. al., *J. Neurochemistry*, 91(6) 1249-59 (2004)). The content is mixed well on a plate shaker for 10 minutes. Fifteen µL of two hundred pM human BACE(1-460):Fc (See Vasser, et al., *Science*, 286, 735-741 (1999)) in the $KH_2PO_4$ buffer is added to the plate containing substrate and test compounds to initiate the reaction. The RFU of the mixture at time 0 is recorded at excitation wavelength 355 nm and emission wavelength 460 nm, after brief mixing on a plate shaker. The reaction plate is covered with aluminum foil and kept in a dark humidified oven at room temperature for 16 to 24 h. The RFU at the end of incubation is recorded with the same excitation and emission setting. The difference of the RFU at time 0 and the end of incubation is representative of the activity of BACE under the compound treatment. RFU differences are plotted versus inhibitor concentration and a curve is fitted with a four-parameter logistic equation to obtain the $EC_{50}$ and $IC_{50}$ values. (See Sinha, et al., *Nature*, 402, 537-540 (2000)).

The compounds exemplified herein were tested essentially as described above and exhibited an $IC_{50}$ value for BACE of lower than 1 µM. The following exemplified compounds were tested essentially as described above and exhibited the following activity for BACE:

TABLE 26

| EXAMPLE | BACE $IC_{50}$ (nM) |
|---|---|
| 5 | 239 |
| 19 | 420 |
| 12 | 833 |
| 21 | 867 |

These data demonstrate that the compounds of Table 26 inhibit purified recombinant BACE enzyme activity in vitro.

Expression of Human BACE

Human (accession number: AF190725) is cloned from total brain cDNA by room temperature-PCR. The nucleotide sequences corresponding to amino acid sequences #1 to 460 are inserted into the cDNA encoding human $IgG_1$ (Fc) polypeptide (Vassar et al. 1999). This fusion protein of BACE (1-460) and human Fc, named huBACE:Fc, is constructed into the pJB02 vector. Human BACE(1-460):Fc (huBACE:Fc) is transiently expressed in HEK293 cells. 250 µg cDNA of each construct is mixed with Fugene 6 and added to 1 liter HEK293 cells. Four days after the transfection, conditioned media are harvested for purification.

Purification of huBACE:Fc huBACE:Fc is purified by Protein A chromatography. The enzyme is stored at −80° C. in small aliquots.

Whole Cell Assays for Measuring the Inhibition of Beta-Secretase Activity

HEK293Swe Whole Cell Assay

The routine whole cell assay for the measurement of inhibition of beta-secretase activity utilizes the human embryonic kidney cell line HEK293p (ATCC Accession No. CRL-1573) stably expressing a human APP751 cDNA containing the naturally occurring double mutation Lys651Met652 to Asn652Leu652, commonly called the Swedish mutation (noted HEK293/APP751sw) and shown to overproduce Abeta (Citron, et al., *Nature*, 360, 672-674 (1992)). In vitro Aβ reduction assays have been described in the literature (See Dovey, et al., *Journal of Neurochemistry*, 76, 173-181 (2001); Seubert, et al., *Nature*, 361, 260 (1993); and Johnson-Wood, et al., *Proc. Natl. Acad. Sci. USA*, 94, 1550-1555 (1997)).

Cells (HEK293/APP751sw at $3.5 \times 10^4$ cells/well, containing 200 µL culture media, DMEM containing 10% FBS) are incubated at 37° C. for 4 to 24 h in the presence/absence of inhibitors (diluted in DMSO) at the desired concentration. At the end of the incubation, conditioned media are analyzed for evidence of beta-secretase activity, for example, by analysis of Abeta peptides. Total Abeta peptides (Abeta 1-x) are measured by a sandwich ELISA, using monoclonal 266 as a capture antibody and biotinylated 3D6 as reporting antibody. Alternatively, Abeta 1-40 and Abeta 1-42 peptides are measured by a sandwich ELISA, using monoclonal 2G3 as a capture antibody for Abeta 1-40, and monoclonal 21F12 as a capture antibody for Abeta 1-42. Both Abeta 1-40 and Abeta 1-42 ELISAs use biotinylated 3D6 as the reporting antibody. The concentration of Abeta released in the conditioned media following the compound treatment corresponds to the activity of BACE under such conditions. The 10-point inhibition curve is plotted and fitted with the four-parameter logistic equation to obtain the $EC_{50}$ and $IC_{50}$ values for the Abeta-lowering effect. The following exemplified compounds were tested essentially as described above and exhibited the following activity for Abeta lowering effect:

TABLE 27

| EXAMPLE | HEK 293 Swe A-beta (1-40) ELISA $IC_{50}$ (nM) | HEK 293 Swe A-beta (1-42) ELISA $IC_{50}$ (nM) |
|---|---|---|
| 5 | 303 | 299 |
| 19 | 335 | 480 |
| 12 | 1300 | 948 |
| 21 | 863 | 803 |

These data demonstrate that the compounds of Table 27 inhibit native endogenous human BACE in cells in vitro.

PDAPP Primary Neuronal Assay

A confirmatory whole cell assay is also run in primary neuronal cultures generated from PDAPP transgenic embryonic mice. Primary cortical neurons are prepared from Embryonic Day 16 PDAPP embryos and cultured in 96 well plates ($15 \times 10^4$ cells/well in DMEM/F12 (1:1) plus 10% FBS). After 4-6 days in vitro, culture media is replaced with serum free DMEM/F12 (1:1) containing B27 supplement and neurons are incubated at 37° C. for 24 h in the presence/absence of inhibitors (diluted in DMSO) at the desired concentration. At the end of the incubation, conditioned media are analyzed for evidence of beta-secretase activity, for example, by analysis of Abeta peptides. Total Abeta peptides (Abeta 1-x) are measured by a sandwich ELISA, using monoclonal 266 as a capture antibody and biotinylated 3D6 as reporting antibody. Alternatively, Abeta 1-40 and Abeta 1-42 peptides are measured by a sandwich ELISA, using monoclonal 2G3 as a capture antibody for Abeta 1-40, and monoclonal 21F12 as a capture antibody for Abeta 1-42. Both Abeta 1-40 and Abeta 1-42 ELISAs use biotinylated 3D6 as the reporting antibody. The concentration of Abeta released in the conditioned media following the compound treatment corresponds to the activity of BACE under such conditions. The 10-point inhibition curve is plotted and fitted with the four-parameter logistic equation to obtain the $EC_{50}$ and $IC_{50}$ values for the Abeta-lowering effect. The following exemplified compounds were tested essentially as described above and exhibited the following activity for Abeta lowering effect:

TABLE 28

| EXAMPLE | PDAPP Neuron A-beta (1-40) ELISA $IC_{50}$ (nM) | PDAPP Neuron A-beta (1-42) ELISA $IC_{50}$ (nM) |
|---|---|---|
| 5 | 102 | 94.7 |
| 19 | 288 | 214 |
| 12 | 658 | 648 |
| 21 | 355 | 429 |

These data demonstrate that the compounds of Table 28 inhibit native, endogenous murine BACE in cells in vitro.

In Vivo Inhibition of Beta-Secretase

Several animal models, including mouse, guinea pig, dog, and monkey, may be used to screen for inhibition of beta-secretase activity in vivo following compound treatment. Animals used in this invention can be wild type, transgenic, or gene knockout animals. For example, the PDAPP mouse model, prepared as described in Games et al., Nature 373, 523-527 (1995), and other non-transgenic or gene knockout animals are useful to analyze in vivo inhibition of Abeta and sAPPbeta production in the presence of inhibitory compounds. Generally, 2 to 12 month old PDAPP mice, gene knockout mice or non-transgenic animals are administered compound formulated in vehicles, such as corn oil, cyclodextran, phosphate buffers, PHARMASOLVE®, or other suitable vehicles. One to twenty-four hours following the administration of compound, animals are sacrificed, and brains as well as cerebrospinal fluid and plasma are removed for analysis of Abetas, C99 and sAPP fragments. (See Dovey, et al., Journal of Neurochemistry, 76, 173-181 (2001); and Johnson-Wood, et al., Proc. Natl. Acad. Sci. USA, 94, 1550-1555 (1997)).

For standard efficacy studies, animals are dosed with various concentrations of compound and compared to a vehicle-treated control group dosed at the same time. For some time course studies, brain tissue, plasma or cerebrospinal fluid is obtained from selected animals, beginning at time 0 to establish a baseline. Compound is administered to other groups and sacrificed at various times after dosing. Brain tissue, plasma or cerebrospinal fluid is obtained from selected animals and analyzed for the presence of APP cleavage products, including Abeta peptides, sAPPbeta and other APP fragments, for example, by specific sandwich ELISA assays. At the end of the test period, animals are sacrificed and brain tissues, plasma or cerebrospinal fluid are analyzed for the presence of Abeta peptides, C99 and sAPPbeta. Brain tissues of APP transgenic animals are also analyzed for the amount of beta-amyloid plaques following compound treatment.

Animals (PDAPP or other APP transgenic or non-transgenic mice) administered an inhibitory compound may demonstrate the reduction of Abeta or sAPPbeta in brain tissues, plasma or cerebrospinal fluids and decrease of beta amyloid plaques in brain tissue, as compared with vehicle-treated controls or Time Zero controls. For example, 3 hours after administration of 100 mg/kg sub-cutaneous dose of the compound of example 19 to young male PDAPP mice, Abeta 1-x peptide, C99 and sAPPb levels are reduced approximately 30%, 50% and 20% in brain cortex, respectively, compared to vehicle-treated mice. Similarly, 3 hours after administration of a 30 mg/kg sub-cutaneous dose of the compound of example 5 to young male PDAPP mice, Abeta 1-x peptide, C99 and sAPPb levels are reduced approximately 50%, 45% and 30%, respectively, compared to vehicle-treated mice. Consistent with changes in brain Abeta, C99 and sAPPb, 3 hours after oral administration of a 10 mg/kg dose of the compound of example 5, plasma and CSF Abeta 1-x levels are reduced by approximately 50% and 60%, respectively.

A compound exemplified in WO 2007/049532 and its enantiomers were tested as essentially described in the above assays and exhibit the following activities:

TABLE 29[17]

| Structure | BACE | HEK 293 Swe A-beta (1-40) ELISA | HEK 293 Swe A-beta (1-42) ELISA | PDAPP Neuron A-beta (1-40) ELISA | PDAPP Neuron A-beta (1-42) ELISA |
|---|---|---|---|---|---|
| (structure) HCl | 116,000 | 21,400 | 35,300 | | |
| (structure) HCl | 28,000 | 13,200 | 16,400 | 7,820 | 10,400 |
| (structure) HCl | >100,000 | 16,500 | 23,700 | 28,100 | 46,800 |

[17]All data in Table 29 are reported as $IC_{50}$ (nM).

The compounds of the present invention are preferably formulated as pharmaceutical compositions administered by a variety of routes. Most preferably, such compounds are for oral administration. Such pharmaceutical compositions and processes for preparing same are well known in the art. See, e.g., Remington: *The Science and Practice of Pharmacy* (A. Gennaro, et. al., eds., 19th ed., Mack Publishing Co., 1995).

The compounds of Formula I are generally effective over a wide dosage range. For example, dosages per day normally fall within the range of about 0.01 to about 30 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

We claim:

1. A compound of Formula I:

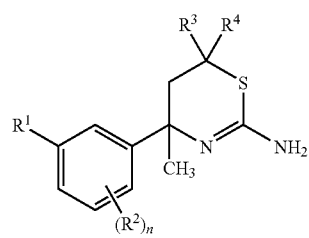

where:

n is 0, 1, or 2;

$R^1$ is pyrimidinyl, pyrazinyl optionally substituted with chloro or fluoro, or pyridinyl optionally substituted with one or two substituents each independently selected from chloro, fluoro, and $C_1$-$C_3$ alkoxy;

$R^2$ is at each instance independently selected from chloro or fluoro;

R³ is hydrogen or C₁-C₄ alkyl optionally substituted with hydroxy; and
R⁴ is hydrogen or C₁-C₃ alkyl;
or a pharmaceutically acceptable salt thereof.

2. A compound of claim 1 wherein R¹ is pyrimidinyl, pyridinyl optionally substituted one or two times at each instance independently selected from chloro, fluoro, or methoxy, or pyrazinyl optionally substituted with fluoro; R² is chloro or fluoro; R³ is hydrogen, methyl, methyl substituted with hydroxy, or iso-propyl substituted with hydroxy; R⁴ is hydrogen; and n is 0, 1 or 2; or a pharmaceutically acceptable salt thereof.

3. A compound of claim 1 wherein R¹ is pyrimidinyl, pyridinyl optionally substituted with fluoro, or pyrazinyl optionally substituted with fluoro; R² is fluoro; R³ is hydrogen or methyl; R⁴ is hydrogen; and n is 1 or 2; or a pharmaceutically acceptable salt thereof.

4. A compound of claim 1 wherein R¹ is pyrimidinyl, R² is fluoro, R³ is hydrogen, R⁴ is hydrogen, and n is 2, or a pharmaceutically acceptable salt thereof.

5. A compound of claim 1 wherein the configuration of the chiral center adjacent to the nitrogen of the aminothiazine is (S), or a pharmaceutically acceptable salt thereof.

6. The compound 4-(2,4-difluoro-5-(pyrimidin-5-yl)phenyl)-4-methyl-5,6-dihydro-4H-1,3-thiazin-2-amine:

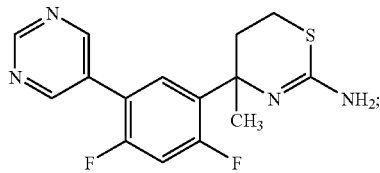

or a pharmaceutically acceptable salt thereof.

7. A compound of claim 6 wherein the compound is (S)-4-(2,4-difluoro-5-(pyrimidin-5-yl)phenyl)-4-methyl-5,6-dihydro-4H-1,3-thiazin-2-amine:

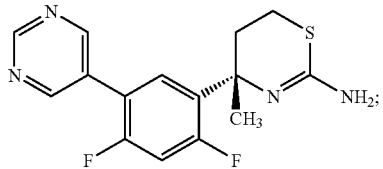

or a pharmaceutically acceptable salt thereof.

8. A pharmaceutical formulation comprising a compound of claim 1, or a pharmaceutically acceptable salt thereof, in combination with a pharmaceutically acceptable carrier, diluent, or excipient.

9. A pharmaceutical formulation comprising a compound of claim 6, or a pharmaceutically acceptable salt thereof, in combination with a pharmaceutically acceptable carrier, diluent, or excipient.

10. A pharmaceutical formulation comprising a compound of claim 7, or a pharmaceutically acceptable salt thereof, in combination with a pharmaceutically acceptable carrier, diluent, or excipient.

11. A method for treating Alzheimer's disease by administering an effective amount of a compound of claim 1, or a pharmaceutically acceptable salt thereof.

12. A method for treating Alzheimer's disease by administering an effective amount of a compound of claim 6, or a pharmaceutically acceptable salt thereof.

13. A method for treating Alzheimer's disease by administering an effective amount of a compound of claim 7, or a pharmaceutically acceptable salt thereof.

* * * * *